(12) United States Patent
Di Maiuta et al.

(10) Patent No.: US 10,415,098 B2
(45) Date of Patent: Sep. 17, 2019

(54) NUCLEIC ACIDS AND METHODS FOR DETECTING PATHOGENS AND BENEFICIAL MICROORGANISMS

(71) Applicant: Omya International AG, Oftringen (CH)

(72) Inventors: Nicola Di Maiuta, Zuchwil (CH); Konrad Egli, Olten (CH); Joachim Glaubitz, Sins (CH); Simon Urwyler, Bern (CH)

( * ) Notice: Subject to any disclaimer, the term of this patent is extended or adjusted under 35 U.S.C. 154(b) by 85 days.

(21) Appl. No.: 15/032,325

(22) PCT Filed: Nov. 5, 2014

(86) PCT No.: PCT/EP2014/073768
§ 371 (c)(1),
(2) Date: Apr. 27, 2016

(87) PCT Pub. No.: WO2015/067635
PCT Pub. Date: May 14, 2015

(65) Prior Publication Data
US 2016/0258000 A1    Sep. 8, 2016

(30) Foreign Application Priority Data
Nov. 6, 2013 (EP) .................... 13191823

(51) Int. Cl.
*C12Q 1/689* (2018.01)
*C12Q 1/6895* (2018.01)

(52) U.S. Cl.
CPC .......... *C12Q 1/689* (2013.01); *C12Q 1/6895* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| 6,274,373 | B1 * | 8/2001 | Virtanen | B01J 19/0046 |
| | | | | 435/283.1 |
| 2001/0053519 | A1 * | 12/2001 | Fodor | B01J 19/0046 |
| | | | | 435/6.11 |
| 2011/0111970 | A1 | 5/2011 | Tzean et al. | |
| 2011/0152385 | A1 * | 6/2011 | Di Maiuta | C12Q 1/6895 |
| | | | | 514/789 |
| 2013/0023445 | A1 * | 1/2013 | Zhang | C12Q 1/6837 |
| | | | | 506/16 |

FOREIGN PATENT DOCUMENTS

| EP | 2130928 A1 | 12/2009 |
| WO | 2009147017 A1 | 12/2009 |

OTHER PUBLICATIONS

Communication dated Apr. 9, 2014 with extended Search Report for European Application No. EP13191823.7.
Lin "Rapid detection and identification of the free-living nitrogen fixing genus *Azospirillum* by 16S rRNA-gene-targeted genus-specific primers." Antonie van Leeuwenhoek (2011) 99:837-844.
Aguin "In vitro selection of an effective fungicide against Armillaria mellea and control of white root rot of grapevine in the field." Pest Management Science 62:223-228 (2006).
Sicoli "Development of species-specific PCR primers on rDNA for the identification of European *Armillaria* species." For. Path. 33 (2003) 287-297.
Published International Search Report dated May 14, 2015 for PCT Application No. PCT/EP2014/073768.
Written Opinion of the International Searching Authority dated Apr. 29, 2015 for PCT Application No. PCT/EP2014/073768.

* cited by examiner

*Primary Examiner* — Joseph G. Dauner
(74) *Attorney, Agent, or Firm* — Heslin Rothenberg Farley & Mesiti P.C.

(57) ABSTRACT

The present invention relates to nucleic acids and methods for detecting pathogens and beneficial microorganisms.

28 Claims, No Drawings

Specification includes a Sequence Listing.

```
                    SEQUENCE LISTING

<160> NUMBER OF SEQ ID NOS: 104

<210> SEQ ID NO 1
<211> LENGTH: 22
<212> TYPE: DNA
<213> ORGANISM: Armillaria mellea

<400> SEQUENCE: 1
gggttgcttg cttgcgagct cc                                              22

<210> SEQ ID NO 2
<211> LENGTH: 25
<212> TYPE: DNA
<213> ORGANISM: Artificial Sequence
<220> FEATURE:
<223> OTHER INFORMATION: Ascochyta phleina

<400> SEQUENCE: 2
```

-continued

```
ctggtgtttg gactcgcctt aaaac                                            25

<210> SEQ ID NO 3
<211> LENGTH: 26
<212> TYPE: DNA
<213> ORGANISM: Artificial Sequence
<220> FEATURE:
<223> OTHER INFORMATION: Bipolaris sorokiniana

<400> SEQUENCE: 3
gcacatattt tgcgctttgt atcagg                                           26

<210> SEQ ID NO 4
<211> LENGTH: 24
<212> TYPE: DNA
<213> ORGANISM: Artificial Sequence
<220> FEATURE:
<223> OTHER INFORMATION: Blumeria graminis

<400> SEQUENCE: 4
tccgccaggg aaraccaaaa ctct                                             24

<210> SEQ ID NO 5
<211> LENGTH: 19
<212> TYPE: DNA
<213> ORGANISM: Artificial Sequence
<220> FEATURE:
<223> OTHER INFORMATION: Cercospora zebrina

<400> SEQUENCE: 5
cggagcgcgg gccgtcgcg                                                   19

<210> SEQ ID NO 6
<211> LENGTH: 24
<212> TYPE: DNA
<213> ORGANISM: Artificial Sequence
<220> FEATURE:
<223> OTHER INFORMATION: Claviceps purpurea

<400> SEQUENCE: 6
acttataccc aaaacgttgc ctcg                                             24

<210> SEQ ID NO 7
<211> LENGTH: 25
<212> TYPE: DNA
<213> ORGANISM: Artificial Sequence
<220> FEATURE:
<223> OTHER INFORMATION: Colletotrichum trifolii

<400> SEQUENCE: 7
cattatcgag tttacgctcc ataac                                            25

<210> SEQ ID NO 8
<211> LENGTH: 23
<212> TYPE: DNA
<213> ORGANISM: Artificial Sequence
<220> FEATURE:
<223> OTHER INFORMATION: Corticium fuciforme

<400> SEQUENCE: 8
gcgcagctat tagatctacg gtg                                              23

<210> SEQ ID NO 9
<211> LENGTH: 26
<212> TYPE: DNA
<213> ORGANISM: Artificial Sequence
```

```
<220> FEATURE:
<223> OTHER INFORMATION: Curvularia affinis

<400> SEQUENCE: 9
gcaaggctgg agtattttat taccct                                          26

<210> SEQ ID NO 10
<211> LENGTH: 22
<212> TYPE: DNA
<213> ORGANISM: Artificial Sequence
<220> FEATURE:
<223> OTHER INFORMATION: Drechslera dictyoides

<400> SEQUENCE: 10
ccgtggcctt gttgccacgc cc                                              22

<210> SEQ ID NO 11
<211> LENGTH: 23
<212> TYPE: DNA
<213> ORGANISM: Artificial Sequence
<220> FEATURE:
<223> OTHER INFORMATION: Drechslera phlei

<400> SEQUENCE: 11
attggggcct tgttgccaca ccc                                             23

<210> SEQ ID NO 12
<211> LENGTH: 23
<212> TYPE: DNA
<213> ORGANISM: Artificial Sequence
<220> FEATURE:
<223> OTHER INFORMATION: Drechslera poae

<400> SEQUENCE: 12
ttttgcgctt tgtccagttg cgg                                             23

<210> SEQ ID NO 13
<211> LENGTH: 22
<212> TYPE: DNA
<213> ORGANISM: Artificial Sequence
<220> FEATURE:
<223> OTHER INFORMATION: Drechslera siccans

<400> SEQUENCE: 13
gattcgtcgc cccccctcct gg                                              22

<210> SEQ ID NO 14
<211> LENGTH: 27
<212> TYPE: DNA
<213> ORGANISM: Artificial Sequence
<220> FEATURE:
<223> OTHER INFORMATION: Drechslera tritici-repentis

<400> SEQUENCE: 14
gaccttattc aaacctttt ttcagtt                                          27

<210> SEQ ID NO 15
<211> LENGTH: 23
<212> TYPE: DNA
<213> ORGANISM: Artificial Sequence
<220> FEATURE:
<223> OTHER INFORMATION: Epichloe typhina

<400> SEQUENCE: 15
gctgttgggg accggctcac ccg                                             23
```

<210> SEQ ID NO 16
<211> LENGTH: 26
<212> TYPE: DNA
<213> ORGANISM: Artificial Sequence
<220> FEATURE:
<223> OTHER INFORMATION: Exserohilum turcicum

<400> SEQUENCE: 16
tgaccgttgt cacgagacga cttttat                                         26

<210> SEQ ID NO 17
<211> LENGTH: 23
<212> TYPE: DNA
<213> ORGANISM: Artificial Sequence
<220> FEATURE:
<223> OTHER INFORMATION: Fusarium culmorum

<400> SEQUENCE: 17
cttggtgttg ggagctgcag tcc 23

<210> SEQ ID NO 18
<211> LENGTH: 22
<212> TYPE: DNA
<213> ORGANISM: Artificial Sequence
<220> FEATURE:
<223> OTHER INFORMATION: Fusarium poae

<400> SEQUENCE: 18
ccattgcgta gtagtaaaac cc 22

<210> SEQ ID NO 19
<211> LENGTH: 22
<212> TYPE: DNA
<213> ORGANISM: Artificial Sequence
<220> FEATURE:
<223> OTHER INFORMATION: Gaeumannomyces graminis

<400> SEQUENCE: 19
aacgcgcttc gttcggaggc tt 22

<210> SEQ ID NO 20
<211> LENGTH: 25
<212> TYPE: DNA
<213> ORGANISM: Artificial Sequence
<220> FEATURE:
<223> OTHER INFORMATION: Gibberella intermedia

<400> SEQUENCE: 20
ttcaaccctc aagcccccgg gtttg 25

<210> SEQ ID NO 21
<211> LENGTH: 24
<212> TYPE: DNA
<213> ORGANISM: Artificial Sequence
<220> FEATURE:
<223> OTHER INFORMATION: Gliocladium catenulatum

<400> SEQUENCE: 21
cgaagtagtg atattccgca tcgg 24

<210> SEQ ID NO 22
<211> LENGTH: 21
<212> TYPE: DNA
<213> ORGANISM: Glomerella graminicola

<400> SEQUENCE: 22

-continued

```
gttaggggt cccctctccg g                                          21

<210> SEQ ID NO 23
<211> LENGTH: 19
<212> TYPE: DNA
<213> ORGANISM: Artificial Sequence
<220> FEATURE:
<223> OTHER INFORMATION: Kabatiella caulivora

<400> SEQUENCE: 23
ctcggtctcg agccgccgg                                            19

<210> SEQ ID NO 24
<211> LENGTH: 28
<212> TYPE: DNA
<213> ORGANISM: Artificial Sequence
<220> FEATURE:
<223> OTHER INFORMATION: Leptosphaeria korrae

<400> SEQUENCE: 24
acaccccatt gaacctattt attttyaa                                  28

<210> SEQ ID NO 25
<211> LENGTH: 24
<212> TYPE: DNA
<213> ORGANISM: Artificial Sequence
<220> FEATURE:
<223> OTHER INFORMATION: Leptosphaerulina australis

<400> SEQUENCE: 25
acatctcgcg ctttgcattc agaa                                      24

<210> SEQ ID NO 26
<211> LENGTH: 23
<212> TYPE: DNA
<213> ORGANISM: Artificial Sequence
<220> FEATURE:
<223> OTHER INFORMATION: Macrophomina phaseolina

<400> SEQUENCE: 26
cgattttggg gggtggctag tgc                                       23

<210> SEQ ID NO 27
<211> LENGTH: 25
<212> TYPE: DNA
<213> ORGANISM: Artificial Sequence
<220> FEATURE:
<223> OTHER INFORMATION: Magnaporthe poae

<400> SEQUENCE: 27
ctctgagtac gaaagaacc tgaaa                                      25

<210> SEQ ID NO 28
<211> LENGTH: 24
<212> TYPE: DNA
<213> ORGANISM: Artificial Sequence
<220> FEATURE:
<223> OTHER INFORMATION: Marasmius oreades

<400> SEQUENCE: 28
tgctggctct tctagagtcg gctc                                      24

<210> SEQ ID NO 29
<211> LENGTH: 22
<212> TYPE: DNA
```

<213> ORGANISM: Artificial Sequence
<220> FEATURE:
<223> OTHER INFORMATION: Microdochium bolleyi

<400> SEQUENCE: 29
ggccagacga cagccataaa cc                                            22

<210> SEQ ID NO 30
<211> LENGTH: 23
<212> TYPE: DNA
<213> ORGANISM: Artificial Sequence
<220> FEATURE:
<223> OTHER INFORMATION: Microdochium nivale

<400> SEQUENCE: 30
cgccggtgga ctacctaaac tct                                           23

<210> SEQ ID NO 31
<211> LENGTH: 22
<212> TYPE: DNA
<213> ORGANISM: Artificial Sequence
<220> FEATURE:
<223> OTHER INFORMATION: Microsphaera trifolii

<400> SEQUENCE: 31
cgtcgtcgct gttcgcaagg ac                                            22

<210> SEQ ID NO 32
<211> LENGTH: 21
<212> TYPE: DNA
<213> ORGANISM: Artificial Sequence
<220> FEATURE:
<223> OTHER INFORMATION: Myrothecium roridum

<400> SEQUENCE: 32
tcgggcaacg gaaccaggcg c                                             21

<210> SEQ ID NO 33
<211> LENGTH: 20
<212> TYPE: DNA
<213> ORGANISM: Artificial Sequence
<220> FEATURE:
<223> OTHER INFORMATION: Neotyphodium sp.

<400> SEQUENCE: 33
gttgcctcgg cgggcacggc                                               20

<210> SEQ ID NO 34
<211> LENGTH: 26
<212> TYPE: DNA
<213> ORGANISM: Artificial Sequence
<220> FEATURE:
<223> OTHER INFORMATION: Ophiosphaerella herpotricha

<400> SEQUENCE: 34
ccagttatat aggcacccaa taagcc                                        26

<210> SEQ ID NO 35
<211> LENGTH: 24
<212> TYPE: DNA
<213> ORGANISM: Artificial Sequence
<220> FEATURE:
<223> OTHER INFORMATION: Ophiosphaerella narmari

<400> SEQUENCE: 35
caccaaacca gcttgggaaa cctt                                          24

<210> SEQ ID NO 36
<211> LENGTH: 22
<212> TYPE: DNA
<213> ORGANISM: Artificial Sequence
<220> FEATURE:
<223> OTHER INFORMATION: Peronospora trifoliorum

<400> SEQUENCE: 36
gtcacgtggt cttggttttg aa                                          22

<210> SEQ ID NO 37
<211> LENGTH: 23
<212> TYPE: DNA
<213> ORGANISM: Artificial Sequence
<220> FEATURE:
<223> OTHER INFORMATION: Phyllachora vulgata

<400> SEQUENCE: 37
cgcaaccggg agccgcggcg cgg                                         23

<210> SEQ ID NO 38
<211> LENGTH: 23
<212> TYPE: DNA
<213> ORGANISM: Artificial Sequence
<220> FEATURE:
<223> OTHER INFORMATION: Phytophthora brassicae

<400> SEQUENCE: 38
tggactggct tcggctagac tgg                                         23

<210> SEQ ID NO 39
<211> LENGTH: 25
<212> TYPE: DNA
<213> ORGANISM: Phytophthora cactorum

<400> SEQUENCE: 39
accatagctc agttgcttgg ctttt                                       25

<210> SEQ ID NO 40
<211> LENGTH: 24
<212> TYPE: DNA
<213> ORGANISM: Phytophthora citricola

<400> SEQUENCE: 40
tggcgaatgt ttggacttcg gtct                                        24

<210> SEQ ID NO 41
<211> LENGTH: 21
<212> TYPE: DNA
<213> ORGANISM: Phytophthora drechsleri

<400> SEQUENCE: 41
gcgcaagctg gggtggrcga g                                           21

<210> SEQ ID NO 42
<211> LENGTH: 22
<212> TYPE: DNA
<213> ORGANISM: Phytophthora fragariae

<400> SEQUENCE: 42
gaacttgtgt ctctgcggcg cg                                          22

<210> SEQ ID NO 43

```
<211> LENGTH: 25
<212> TYPE: DNA
<213> ORGANISM: Phytophthora megasperma

<400> SEQUENCE: 43
aactggtgaa ccgtagctgt gtggt                                             25

<210> SEQ ID NO 44
<211> LENGTH: 26
<212> TYPE: DNA
<213> ORGANISM: Artificial Sequence
<220> FEATURE:
<223> OTHER INFORMATION: Phytophthora nicotianae

<400> SEQUENCE: 44
ccgtacatta aacttgactt tcttcc                                            26

<210> SEQ ID NO 45
<211> LENGTH: 24
<212> TYPE: DNA
<213> ORGANISM: Artificial Sequence
<220> FEATURE:
<223> OTHER INFORMATION: Pseudopeziza medicaginis

<400> SEQUENCE: 45
ggaactccac ccttgaatac actg                                              24

<210> SEQ ID NO 46
<211> LENGTH: 25
<212> TYPE: DNA
<213> ORGANISM: Puccinia coronata

<400> SEQUENCE: 46
cgaccccttt tataattcac ccaac                                             25

<210> SEQ ID NO 47
<211> LENGTH: 27
<212> TYPE: DNA
<213> ORGANISM: Puccinia coronata

<400> SEQUENCE: 47
ctaaaaaacc cctcataacc tttttt                                            27

<210> SEQ ID NO 48
<211> LENGTH: 29
<212> TYPE: DNA
<213> ORGANISM: Puccinia graminis

<400> SEQUENCE: 48
ctcctaaaac ccaatatctt atttttaag                                         29

<210> SEQ ID NO 49
<211> LENGTH: 26
<212> TYPE: DNA
<213> ORGANISM: Artificial Sequence
<220> FEATURE:
<223> OTHER INFORMATION: Puccinia poae-nemoralis

<400> SEQUENCE: 49
caatactgcc atcttgtttt tgaagg                                            26

<210> SEQ ID NO 50
<211> LENGTH: 23
<212> TYPE: DNA
<213> ORGANISM: Puccinia poarum
```

```
<400> SEQUENCE: 50
atacttgcca tcttttgga agg                                           23

<210> SEQ ID NO 51
<211> LENGTH: 20
<212> TYPE: DNA
<213> ORGANISM: Puccinia recondita

<400> SEQUENCE: 51
cctaaaaacc cccttatca                                               20

<210> SEQ ID NO 52
<211> LENGTH: 26
<212> TYPE: DNA
<213> ORGANISM: Puccinia sorghi

<400> SEQUENCE: 52
caaccttttt ggagtattct aatgat                                       26

<210> SEQ ID NO 53
<211> LENGTH: 26
<212> TYPE: DNA
<213> ORGANISM: Puccinia striiformis

<400> SEQUENCE: 53
atactgccat cttattkaag ggagac                                       26

<210> SEQ ID NO 54
<211> LENGTH: 21
<212> TYPE: DNA
<213> ORGANISM: Artificial Sequence
<220> FEATURE:
<223> OTHER INFORMATION: Puccinia triticina

<400> SEQUENCE: 54
cagggctatc ccctgccag g                                             21

<210> SEQ ID NO 55
<211> LENGTH: 24
<212> TYPE: DNA
<213> ORGANISM: Artificial Sequence
<220> FEATURE:
<223> OTHER INFORMATION: Pyrenochaeta lycopersici

<400> SEQUENCE: 55
ggagggttgc gcactttgtg cgtg                                         24

<210> SEQ ID NO 56
<211> LENGTH: 22
<212> TYPE: DNA
<213> ORGANISM: Artificial Sequence
<220> FEATURE:
<223> OTHER INFORMATION: Pythium aphanidermatuma

<400> SEQUENCE: 56
gacgccctgt tttcggatag gg                                           22

<210> SEQ ID NO 57
<211> LENGTH: 23
<212> TYPE: DNA
<213> ORGANISM: Artificial Sequence
<220> FEATURE:
<223> OTHER INFORMATION: Pythium debaryanum
```

<400> SEQUENCE: 57
tggcgtgcgt tgcttgcgc ttc                                    23

<210> SEQ ID NO 58
<211> LENGTH: 27
<212> TYPE: DNA
<213> ORGANISM: Artificial Sequence
<220> FEATURE:
<223> OTHER INFORMATION: Pythium graminicola

<400> SEQUENCE: 58
ctatactccg agaacgaaag tttttgg                               27

<210> SEQ ID NO 59
<211> LENGTH: 24
<212> TYPE: DNA
<213> ORGANISM: Pythium irregulare

<400> SEQUENCE: 59
tagtagtgtg tgtrgcacgt tgtc                                  24

<210> SEQ ID NO 60
<211> LENGTH: 29
<212> TYPE: DNA
<213> ORGANISM: Artificial Sequence
<220> FEATURE:
<223> OTHER INFORMATION: Pythium mastophorum

<400> SEQUENCE: 60
tgtttttgtt ttgtggaaat acgctgttt                             29

<210> SEQ ID NO 61
<211> LENGTH: 24
<212> TYPE: DNA
<213> ORGANISM: Artificial Sequence
<220> FEATURE:
<223> OTHER INFORMATION: Pythium sulcatum

<400> SEQUENCE: 61
gtagaatttt gctgctcttg ggcg                                  24

<210> SEQ ID NO 62
<211> LENGTH: 25
<212> TYPE: DNA
<213> ORGANISM: Artificial Sequence
<220> FEATURE:
<223> OTHER INFORMATION: Pythium ultimum

<400> SEQUENCE: 62
ctgtgtagtc agggatggaa tgtgc                                 25

<210> SEQ ID NO 63
<211> LENGTH: 23
<212> TYPE: DNA
<213> ORGANISM: Artificial Sequence
<220> FEATURE:
<223> OTHER INFORMATION: Ramularia collo-cygni

<400> SEQUENCE: 63
tgaacgcatc atgttgcttc ggg                                   23

<210> SEQ ID NO 64
<211> LENGTH: 26
<212> TYPE: DNA
<213> ORGANISM: Artificial Sequence

```
<220> FEATURE:
<223> OTHER INFORMATION: Rhizoctonia cerealis

<400> SEQUENCE: 64
ctggcttttg ttttggattt ggaggt                                26

<210> SEQ ID NO 65
<211> LENGTH: 24
<212> TYPE: DNA
<213> ORGANISM: Artificial Sequence
<220> FEATURE:
<223> OTHER INFORMATION: Rhizoctonia fragariae

<400> SEQUENCE: 65
cagcgacaac cgactctaag ttca                                  24

<210> SEQ ID NO 66
<211> LENGTH: 24
<212> TYPE: DNA
<213> ORGANISM: Artificial Sequence
<220> FEATURE:
<223> OTHER INFORMATION: Rhynchosporium orthosporum

<400> SEQUENCE: 66
ctcgtgaaac acatgaagtc tgag                                  24

<210> SEQ ID NO 67
<211> LENGTH: 22
<212> TYPE: DNA
<213> ORGANISM: Artificial Sequence
<220> FEATURE:
<223> OTHER INFORMATION: Rhynchosporium secalis

<400> SEQUENCE: 67
tcggcgcccc aggagaaatc ct                                    22

<210> SEQ ID NO 68
<211> LENGTH: 22
<212> TYPE: DNA
<213> ORGANISM: Artificial Sequence
<220> FEATURE:
<223> OTHER INFORMATION: Sclerotinia borealis

<400> SEQUENCE: 68
agtccatgtc cgcaatggca gg                                    22

<210> SEQ ID NO 69
<211> LENGTH: 25
<212> TYPE: DNA
<213> ORGANISM: Artificial Sequence
<220> FEATURE:
<223> OTHER INFORMATION: Sclerotinia homoeocarpa

<400> SEQUENCE: 69
aacacatacc tctcgttaca gggtc                                 25

<210> SEQ ID NO 70
<211> LENGTH: 24
<212> TYPE: DNA
<213> ORGANISM: Artificial Sequence
<220> FEATURE:
<223> OTHER INFORMATION: Sclerotinia sclerotiorum

<400> SEQUENCE: 70
gagctgctct tcggggccttt gtat                                 24
```

<210> SEQ ID NO 71
<211> LENGTH: 25
<212> TYPE: DNA
<213> ORGANISM: Artificial Sequence
<220> FEATURE:
<223> OTHER INFORMATION: Sclerotinia trifoliorum

<400> SEQUENCE: 71
cttgtatgcg cgccagagaa tatca                                          25

<210> SEQ ID NO 72
<211> LENGTH: 20
<212> TYPE: DNA
<213> ORGANISM: Artificial Sequence
<220> FEATURE:
<223> OTHER INFORMATION: Septoria macropoda

<400> SEQUENCE: 72
tattgggcgt ccgcggggga                                                20

<210> SEQ ID NO 73
<211> LENGTH: 21
<212> TYPE: DNA
<213> ORGANISM: Artificial Sequence
<220> FEATURE:
<223> OTHER INFORMATION: Septoria tritici

<400> SEQUENCE: 73
gcggagttca cgagccctca c                                              21

<210> SEQ ID NO 74
<211> LENGTH: 21
<212> TYPE: DNA
<213> ORGANISM: Artificial Sequence
<220> FEATURE:
<223> OTHER INFORMATION: Stemphylium sarcinaeforme

<400> SEQUENCE: 74
gcgccttgtc tctcgcgaga c                                              21

<210> SEQ ID NO 75
<211> LENGTH: 25
<212> TYPE: DNA
<213> ORGANISM: Thanatephorus cucumeris

<400> SEQUENCE: 75
agctggatct cagtgttatg cttgg                                          25

<210> SEQ ID NO 76
<211> LENGTH: 22
<212> TYPE: DNA
<213> ORGANISM: Artificial Sequence
<220> FEATURE:
<223> OTHER INFORMATION: Thielaviopsis basicola

<400> SEQUENCE: 76
gtgcctctcg gggcttctgc cg                                             22

<210> SEQ ID NO 77
<211> LENGTH: 26
<212> TYPE: DNA
<213> ORGANISM: Artificial Sequence
<220> FEATURE:
<223> OTHER INFORMATION: Thielaviopsis populi

<400> SEQUENCE: 77
cctgtgtagt aatgcttagc ttacac                                            26

<210> SEQ ID NO 78
<211> LENGTH: 22
<212> TYPE: DNA
<213> ORGANISM: Artificial Sequence
<220> FEATURE:
<223> OTHER INFORMATION: Tilletia caries

<400> SEQUENCE: 78
ctacggaggg gtggctgcgt tg                                                22

<210> SEQ ID NO 79
<211> LENGTH: 22
<212> TYPE: DNA
<213> ORGANISM: Artificial Sequence
<220> FEATURE:
<223> OTHER INFORMATION: Tilletia controversa

<400> SEQUENCE: 79
ctacggaggg gtggctgcgt tg                                                22

<210> SEQ ID NO 80
<211> LENGTH: 26
<212> TYPE: DNA
<213> ORGANISM: Artificial Sequence
<220> FEATURE:
<223> OTHER INFORMATION: Trichoderma hamatum

<400> SEQUENCE: 80
acagctctga gcaaaaattc aaaatg                                            26

<210> SEQ ID NO 81
<211> LENGTH: 22
<212> TYPE: DNA
<213> ORGANISM: Artificial Sequence
<220> FEATURE:
<223> OTHER INFORMATION: Typhula incarnate

<400> SEQUENCE: 81
gtccaatgta ggcgcagcgt aa                                                22

<210> SEQ ID NO 82
<211> LENGTH: 24
<212> TYPE: DNA
<213> ORGANISM: Artificial Sequence
<220> FEATURE:
<223> OTHER INFORMATION: Typhula ishikariensis

<400> SEQUENCE: 82
attagctgga acctcttgtg gacc                                              24

<210> SEQ ID NO 83
<211> LENGTH: 24
<212> TYPE: DNA
<213> ORGANISM: Artificial Sequence
<220> FEATURE:
<223> OTHER INFORMATION: Typhula ishikariensis

<400> SEQUENCE: 83
attagctgga acctcttgtg gacc                                              24

<210> SEQ ID NO 84
<211> LENGTH: 31
<212> TYPE: DNA

```
<213> ORGANISM: Artificial Sequence
<220> FEATURE:
<223> OTHER INFORMATION: Uromyces dactylidis

<400> SEQUENCE: 84
ctcattaaac aatttttct tataaagatt g                               31

<210> SEQ ID NO 85
<211> LENGTH: 26
<212> TYPE: DNA
<213> ORGANISM: Artificial Sequence
<220> FEATURE:
<223> OTHER INFORMATION: Uromyces trifolii-repentis

<400> SEQUENCE: 85
gtcattgcac tcaggtagac gtaaca                                    26

<210> SEQ ID NO 86
<211> LENGTH: 26
<212> TYPE: DNA
<213> ORGANISM: Ustilago maydis

<400> SEQUENCE: 86 ctttttctt ttggaaaagg ttgacg                                     26

<210> SEQ ID NO 87
<211> LENGTH: 26
<212> TYPE: DNA
<213> ORGANISM: Artificial Sequence
<220> FEATURE:
<223> OTHER INFORMATION: Ustilago nuda

<400> SEQUENCE: 87
acagacaatt ttattgaaca cttttt                                    26

<210> SEQ ID NO 88
<211> LENGTH: 24
<212> TYPE: DNA
<213> ORGANISM: Artificial Sequence
<220> FEATURE:
<223> OTHER INFORMATION: Ustilago striiformis

<400> SEQUENCE: 88
tttgaagagt tggcggatcg gtat                                      24

<210> SEQ ID NO 89
<211> LENGTH: 26
<212> TYPE: DNA
<213> ORGANISM: Artificial Sequence
<220> FEATURE:
<223> OTHER INFORMATION: Ustilago tritici

<400> SEQUENCE: 89
acggacaatt ttatttaaca cttttg                                    26

<210> SEQ ID NO 90
<211> LENGTH: 23
<212> TYPE: DNA
<213> ORGANISM: Artificial Sequence
<220> FEATURE:
<223> OTHER INFORMATION: Verticillium dahliae

<400> SEQUENCE: 90
gcccttaaaa kcagtggcgg acc                                       23
```

```
<210> SEQ ID NO 91
<211> LENGTH: 27
<212> TYPE: DNA
<213> ORGANISM: Bacillus amyloliquefaciens

<400> SEQUENCE: 91
taatacatgc aagtcgagcg gacagat                                         27

<210> SEQ ID NO 92
<211> LENGTH: 25
<212> TYPE: DNA
<213> ORGANISM: Artificial Sequence
<220> FEATURE:
<223> OTHER INFORMATION: Pseudomonas chlororaphis

<400> SEQUENCE: 92
gggtacttac ctaatacgtg agtat                                           25

<210> SEQ ID NO 93
<211> LENGTH: 26
<212> TYPE: DNA
<213> ORGANISM: Artificial Sequence
<220> FEATURE:
<223> OTHER INFORMATION: Serratia entomophila

<400> SEQUENCE: 93
gaagggtart gtcttaatac ggcatt                                          26

<210> SEQ ID NO 94
<211> LENGTH: 24
<212> TYPE: DNA
<213> ORGANISM: Artificial Sequence
<220> FEATURE:
<223> OTHER INFORMATION: Serratia plymuthica

<400> SEQUENCE: 94
ggaagggyag tgtgttaata gcac                                            24

<210> SEQ ID NO 95
<211> LENGTH: 24
<212> TYPE: DNA
<213> ORGANISM: Artificial Sequence
<220> FEATURE:
<223> OTHER INFORMATION: Streptomyces albidoflavus

<400> SEQUENCE: 95
atgactgtcc atcgcatggt ggat                                            24

<210> SEQ ID NO 96
<211> LENGTH: 21
<212> TYPE: DNA
<213> ORGANISM: Artificial Sequence
<220> FEATURE:
<223> OTHER INFORMATION: Streptomyces graminofaciens

<400> SEQUENCE: 96
ctgcggatcg catggtctgc g                                               21

<210> SEQ ID NO 97
<211> LENGTH: 24
<212> TYPE: DNA
<213> ORGANISM: Artificial Sequence
<220> FEATURE:
<223> OTHER INFORMATION: Streptomyces griseoviridis

<400> SEQUENCE: 97
```
aatacttctc ctcgcatggg gagg                                          24

<210> SEQ ID NO 98
<211> LENGTH: 24
<212> TYPE: DNA
<213> ORGANISM: Artificial Sequence
<220> FEATURE:
<223> OTHER INFORMATION: Streptomyces rimosus

<400> SEQUENCE: 98
atgacacacg accgcatggt ctgt                                          24

<210> SEQ ID NO 99
<211> LENGTH: 25
<212> TYPE: DNA
<213> ORGANISM: Artificial Sequence
<220> FEATURE:
<223> OTHER INFORMATION: Streptomyces scabiei

<400> SEQUENCE: 99
caccggaaac ggccagagat ggtcg                                         25

<210> SEQ ID NO 100
<211> LENGTH: 23
<212> TYPE: DNA
<213> ORGANISM: Artificial Sequence
<220> FEATURE:
<223> OTHER INFORMATION: Xanthomonas translucens

<400> SEQUENCE: 100
gagtgtggta gaggatggcg gaa                                           23

<210> SEQ ID NO 101
<211> LENGTH: 19
<212> TYPE: DNA
<213> ORGANISM: Artificial Sequence
<220> FEATURE:
<223> OTHER INFORMATION: ITS1 primer

<400> SEQUENCE: 101
tccgtaggtg aacctgcgg                                                19

<210> SEQ ID NO 102
<211> LENGTH: 20
<212> TYPE: DNA
<213> ORGANISM: Artificial Sequence
<220> FEATURE:
<223> OTHER INFORMATION: ITS4 primer

<400> SEQUENCE: 102
tcctccgctt attgatatgc                                               20

<210> SEQ ID NO 103
<211> LENGTH: 20
<212> TYPE: DNA
<213> ORGANISM: Artificial Sequence
<220> FEATURE:
<223> OTHER INFORMATION: EUB8m_f primer

<400> SEQUENCE: 103
agagtttgat cmtggctcag                                               20

<210> SEQ ID NO 104
<211> LENGTH: 19
<212> TYPE: DNA
<213> ORGANISM: Artificial Sequence

```
<220> FEATURE:
<223> OTHER INFORMATION: EUB1088_r primer

<400> SEQUENCE: 104
ctcgttgcgg gacttaacc                                                    19
```

NUCLEIC ACIDS AND METHODS FOR DETECTING PATHOGENS AND BENEFICIAL MICROORGANISMS

CROSS-REFERENCE TO RELATED APPLICATIONS

This is a U.S. national phase of PCT Application No. PCT/EP2014/073768, filed Nov. 5, 2014, which claims priority to European Application No. 13191823.7, filed Nov. 6, 2013.

FIELD OF THE INVENTION

The present invention relates to nucleic acids and methods for detecting pathogens and beneficial microorganisms.

BACKGROUND OF THE INVENTION

Disease in lawn grasses or turfgrasses develops from an interaction among a susceptible plant, an environment favorable for disease development, and a pathogenic organism (fungi and bacteria). Such organisms may also develop on decorative grasses, plants and crops; indeed, they may appear on any suitable organic substrate. Thus, treatment of a diseased substrate, especially turfgrass, usually consists in applying a treatment agent that will either kill the pathogen or keep it from growing.

However, the first step in disease management, and especially turfgrass disease management, should always consist in identifying the causative pathogenic agent. The knowledge of the causative pathogenic agent of a disease is important to select the most appropriate treatment agent (fungicides, bactericides etc.). Indeed, it is important to have identified the disease correctly, so that an appropriate fungicide or bactericide can be selected. Inadequate treatment will not cure the disease and may have a severe effect on the soil and other beneficial organisms. Using the wrong treatment is cost ineffective and may involve the risk of exacerbating the disease, as well as causing other unwanted side effects.

Classical methods for the identification of the causative pathogenic agent essentially rely on the symptoms which can be observed on the individual plant and on the turf stand, as well as on the pathogen structures, which can be found in the vicinity of the diseased turfgrass.

However, these methods may require a long time to be implemented, since they often involve the isolation and the culture of the pathogen in a laboratory. Besides, differentiating closely related pathogen species can be difficult.

Accordingly, molecular biology methods have been developed which circumvent these difficulties. One of the most popular fungal detection methods relies on the Polymerase chain reaction (PCR) amplification of the internal transcribed spacers (1, 2) and the 5.8S rRNA gene (ITS1-5.8S-ITS2) from the fungal rRNA operon (Goodwin et al. (1995) Plant Pathology 44:384-391; Ranjard et al. (2001) Applied and Environmental Microbiology 67:4479-4487).

For bacterial detection, PCR amplification and sequencing of the 16S rRNA gene is used (Nam H R, Lee H M, Lee Y. Isolation of quinupristin/dalfopristin-resistant *Streptococcus agalactiae* from asymptomatic Korean women. J Microbiol. 2008 February; 46(1):108-11. doi: 10.1007/s12275-007-0217-1. PubMed PMID: 18337702).

However, sequencing of the region of a specific primer pair is often necessary for the identification of a given pathogenic species, which renders this method cumbersome where the identity of pathogen is unknown and is sought for. Furthermore, sequencing of mixtures of pathogens is expensive and laborious. Species specific primers to identify certain species out of mixtures are not available for all microorganisms. Accordingly, these methods are not used in routine for determining the anti-pathogenic agent most adapted to treat a given turfgrass disease.

Japanese patent application No. 2008005760 discloses 458 probes for detecting molds that can be found in food. These 458 probes are designed for detecting molds by a hybridization-based method involving the use of a microarray.

Patent application WO 2009/147017 A1, of the same applicant, discloses nucleic acids and methods for detecting pathogenic fungi in turfgrass. This invention relates to turfgrass but focuses on AFLP and T-RFLP as methods for identification. This method has the limit that often many different fungal species, pathogenic and non-pathogenic, are present in turfgrass. Many different species in a complex sample make it difficult or even Impossible identifying numerical underrepresented species. The disease causing pathogenic species, however, is not necessarily the most abundant species.

As a consequence, current methods of choice for the detection of plant pathogens and beneficial microorganisms are time-consuming, not sensitive enough, not specific enough, and/or not broad enough to detect the spectrum of microorganisms.

It is therefore an objective of the present invention to provide specific nucleic acids that enable identification of the pathogens and beneficial microorganisms present in a sample.

It is also an objective of the present invention to provide a single Microarray-Chip containing up to 100 spots with these specific nucleic acids. These nucleic acids are specific for e.g. 90 known fungi and e.g. 10 bacteria species.

A further object of the present invention is a method that enables to test in a single sample for up to 100 different species. Since DNA sequences of very closely related species are identical, this method is also able to include detection of those microorganisms. This method thus makes it possible to screen very fast for many microorganisms. Furthermore, the method is adaptable for high-throughput. The method according to the invention is thus very sensitive and enables detection of pathogens that are present at low levels.

SUMMARY OF THE INVENTION

The present invention arises from the identification, by the inventors, of a selection of nucleotide sequences specific to a conserved region within the gene of rRNA and its intergenic regions of fungi and bacteria generally relevant for turfgrasses' health, but also for other organic substrates.

Thus, the present invention relates to the use of a set of nucleic acids comprising or consisting of:

(i) the sequences selected from the group consisting of:

| | |
|---|---|
| GGGTTGCTTGCTTGCGAGCTCC; | (SEQ ID No 1) |
| CTGGTGTTTGGACTCGCCTTAAAAC; | (SEQ ID No 2) |
| GCACATATTTTGCGCTTTGTATCAGG; | (SEQ ID No 3) |
| TCCGCCAGGGAARACCAAAACTCT; | (SEQ ID No 4) |

-continued

| | |
|---|---|
| CGGAGCGCGGGCCGTCGCG; | (SEQ ID No 5) |
| ACTTATACCCAAAACGTTGCCTCG; | (SEQ ID No 6) |
| CATTATCGAGTTTACGCTCCATAAC; | (SEQ ID No 7) |
| GCGCAGCTATTAGATCTACGGTG; | (SEQ ID No 8) |
| GCAAGGCTGGAGTATTTTATTACCCT; | (SEQ ID No 9) |
| CCGTGGCCTTGTTGCCACGCCC; | (SEQ ID No 10) |
| ATTGGGGCCTTGTTGCCACACCC; | (SEQ ID No 11) |
| TTTTGCGCTTTGTCCAGTTGCGG; | (SEQ ID No 12) |
| GATTCGTCGCCCCCCCTCCTGG; | (SEQ ID No 13) |
| GACCTTATTCAAACCTTTTTTTCAGTT; | (SEQ ID No 14) |
| GCTGTTGGGGACCGGCTCACCCG; | (SEQ ID No 15) |
| TGACCGTTGTCACGAGACGACTTTAT; | (SEQ ID No 16) |
| CTTGGTGTTGGGAGCTGCAGTCC; | (SEQ ID No 17) |
| CCATTGCGTAGTAGTAAAACCC; | (SEQ ID No 18) |
| AACGCGCTTCGTTCGGAGGCTT; | (SEQ ID No 19) |
| TTCAACCCTCAAGCCCCCGGGTTTG; | (SEQ ID No 20) |
| CGAAGTAGTGATATTCCGCATCGG; | (SEQ ID No 21) |
| GTTAGGGGGTCCCCTCTCCGG; | (SEQ ID No 22) |
| CTCGGTCTCGAGCCGCCGG; | (SEQ ID No 23) |
| ACACCCCATTGAACCTATTTATTTTYAA; | (SEQ ID No 24) |
| ACATCTCGCGCTTTGCATTCAGAA; | (SEQ ID No 25) |
| CGATTTTGGGGGGTGGCTAGTGC; | (SEQ ID No 26) |
| CTCTGAGTACGAAAAGAACCTGAAA; | (SEQ ID No 27) |
| TGCTGGCTCTTCTAGAGTCGGCTC; | (SEQ ID No 28) |
| GGCCAGACGACAGCCATAAACC; | (SEQ ID No 29) |
| CGCCGGTGGACTACCTAAACTCT; | (SEQ ID No 30) |
| CGTCGTCGCTGTTCGCAAGGAC; | (SEQ ID No 31) |
| TCGGGCAACGGAACCAGGCGC; | (SEQ ID No 32) |
| GTTGCCTCGGCGGGCACGGC; | (SEQ ID No 33) |
| CCAGTTATATAGGCACCCAATAAGCC; | (SEQ ID No 34) |
| CACCAAACCAGCTTGGGAAACCTT; | (SEQ ID No 35) |
| GTCACGTGGTCTTGGTTTTGAA; | (SEQ ID No 36) |
| CGCAACCGGGAGCCGCGGCGCGG; | (SEQ ID No 37) |
| TGGACTGGCTTCGGCTAGACTGG; | (SEQ ID No 38) |
| ACCATAGCTCAGTTGCTTGGCTTTT; | (SEQ ID No 39) |
| TGGCGAATGTTTGGACTTCGGTCT; | (SEQ ID No 40) |
| GCGCAAGCTGGGGTGGRCGAG; | (SEQ ID No 41) |
| GAACTTGTGTCTCTGCGGCGCG; | (SEQ ID No 42) |
| AACTGGTGAACCGTAGCTGTGTGGT; | (SEQ ID No 43) |
| CCGTACATTAAACTTGACTTTCTTCC; | (SEQ ID No 44) |
| GGAACTCCACCCTTGAATACACTG; | (SEQ ID No 45) |
| CGACCCCTTTTATAATTCACCCAAC; | (SEQ ID No 46) |
| CTAAAAAACCCCTCATAACCTTTTTT; | (SEQ ID No 47) |
| CTCCTAAAACCCAATATCTTATTTTTAAG; | (SEQ ID No 48) |
| CAATACTGCCATCTTGTTTTTGAAGG; | (SEQ ID No 49) |
| ATACTTGCCATCTTTTTGGAAGG; | (SEQ ID No 50) |
| CCTAAAAACCCCCCTTATCA; | (SEQ ID No 51) |
| CAACCTTTTTGGAGTATTCTAATGAT; | (SEQ ID No 52) |
| ATACTGCCATCTTATTKAAGGGAGAC; | (SEQ ID No 53) |
| CAGGGCTATCCCCCTGCCAGG; | (SEQ ID No 54) |
| GGAGGGTTGCGCACTTTGTGCGTG; | (SEQ ID No 55) |
| GACGCCCTGTTTTCGGATAGGG; | (SEQ ID No 56) |
| TGGCGTGCGTTTGCTTGCGCTTC; | (SEQ ID No 57) |
| CTATACTCCGAGAACGAAAGTTTTGG; | (SEQ ID No 58) |
| TAGTAGTGTGTGTRGCACGTTGTC; | (SEQ ID No 59) |
| TGTTTTTGTTTTGTGGAAATACGCTGTTT; | (SEQ ID No 60) |
| GTAGAATTTTGCTGCTCTTGGGCG; | (SEQ ID No 61) |
| CTGTGTAGTCAGGGATGGAATGTGC; | (SEQ ID No 62) |
| TGAACGCATCATGTTGCTTCGGG; | (SEQ ID No 63) |
| CTGGCTTTTGTTTTGGATTTGGAGGT; | (SEQ ID No 64) |
| CAGCGACAACCGACTCTAAGTTCA; | (SEQ ID No 65) |
| CTCGTGAAACACATGAAGTCTGAG; | (SEQ ID No 66) |
| TCGGCGCCCCAGGAGAAATCCT; | (SEQ ID No 67) |
| AGTCCATGTCCGCAATGGCAGG; | (SEQ ID No 68) |
| AACACATACCTCTCGTTACAGGGTC; | (SEQ ID No 69) |
| GAGCTGCTCTTCGGGGCCTTGTAT; | (SEQ ID No 70) |
| CTTGTATGCGCGCCAGAGAATATCA; | (SEQ ID No 71) |
| TATTGGGCGTCCGCGGGGGA; | (SEQ ID No 72) |
| GCGGAGTTCACGAGCCCTCAC; | (SEQ ID No 73) |
| GCGCCTTGTCTCTCGCGAGAC; | (SEQ ID No 74) |
| AGCTGGATCTCAGTGTTATGCTTGG; | (SEQ ID No 75) |
| GTGCCTCTCGGGGCTTCTGCCG; | (SEQ ID No 76) |
| CCTGTGTAGTAATGCTTAGCTTACAC; | (SEQ ID No 77) |
| CTACGGAGGGGTGGCTGCGTTG; | (SEQ ID No 78) |
| CTACGGAGGGGTGGCTGCGTTG; | (SEQ ID No 79) |
| ACAGCTCTGAGCAAAAATTCAAAATG; | (SEQ ID No 80) |
| GTCCAATGTAGGCGCAGCGTAA; | (SEQ ID No 81) |
| ATTAGCTGGAACCTCTTGTGGACC; | (SEQ ID No 82) |
| ATTAGCTGGAACCTCTTGTGGACC; | (SEQ ID No 83) |
| CTCATTAAACAATTTTTTCTTATAAAGATTG; | (SEQ ID No 84) |
| GTCATTGCACTCAGGTAGACGTAACA; | (SEQ ID No 85) |

-continued

| | |
|---|---|
| CTTTTTTCTTTTGGAAAAGGTTGACG; | (SEQ ID No 86) |
| ACAGACAATTTTATTGAACACTTTTT; | (SEQ ID No 87) |
| TTTGAAGAGTTGGCGGATCGGTAT; | (SEQ ID No 88) |
| ACGGACAATTTTATTTAACACTTTTG; | (SEQ ID No 89) |
| GCCCTTAAAAKCAGTGGCGGACC; | (SEQ ID No 90) |
| TAATACATGCAAGTCGAGCGGACAGAT; | (SEQ ID No 91) |
| GGGTACTTACCTAATACGTGAGTAT; | (SEQ ID No 92) |
| GAAGGGTARTGTCTTAATACGGCATT; | (SEQ ID No 93) |
| GGAAGGGYAGTGTGTTAATAGCAC; | (SEQ ID No 94) |
| ATGACTGTCCATCGCATGGTGGAT; | (SEQ ID No 95) |
| CTGCGGATCGCATGGTCTGCG; | (SEQ ID No 96) |
| AATACTTCTCCTCGCATGGGGAGG; | (SEQ ID No 97) |
| ATGACACACGACCGCATGGTCTGT; | (SEQ ID No 98) |
| CACCGGAAACGGCCAGAGATGGTCG; and | (SEQ ID No 99) |
| GAGTGTGGTAGAGGATGGCGGAA; | (SEQ ID No 100) |

(ii) the sequences having at least 80% identity with SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, or (iii) the complementary sequences of (i) or (ii), for the detection by hybridization techniques of at least one pathogen and/or one beneficial microorganism in a sample.

It also relates to a method for detecting by hybridization techniques at least one pathogen and/or one beneficial microorganism in a sample, said method comprising the use of a set of nucleic acids comprising or consisting of:

(i) the sequences selected from the group consisting of SEQ ID No 1; SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, (ii) the sequences having at least 80% identity with SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67 SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, or (iii) the complementary sequences of (i) or (ii).

In one embodiment, the invention also relates to the use of at least one nucleic acid comprising or consisting of:

(i) a sequence selected from the group consisting of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 or SEQ ID No 100, (ii) a sequence having at least 80% identity with SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 or SEQ ID No 100, or (iii) a complementary sequence of (i) or (ii), for the detection by hybridization techniques of at least one pathogen and/or one beneficial microorganism in a sample.

In a particular embodiment, the present invention also relates to a method for detecting by hybridization techniques at least one pathogen and/or one beneficial microorganism in a sample, said method comprising the use of at least one nucleic acid comprising or consisting of:

(i) a sequence selected from the group consisting of SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 or SEQ ID No 100, (ii) a sequence having at least 80% Identity with SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 or SEQ ID No 100, or (iii) the complementary sequences of (i) or (ii).

The present invention also relates to a Microarray-Chip comprising a set of nucleic acids comprising or consisting of:

(i) the sequences SEQ No 1 SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, (ii) the sequences having at least 80% Identity with SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, or (iii) the complementary sequences of (i) or (ii).

In a particular embodiment, the present invention also relates to a Microarray-Chip comprising at least one nucleic acid comprising or consisting of:

(i) a sequence selected from the group consisting of: SEQ No 1 SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, (ii) a sequence having at least 80% identity with SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 or SEQ ID No 100, or (iii) a complementary sequence of (i) or (ii).

The present invention also relates to a detection method of pathogens and/or beneficial microorganisms in an organic sample, comprising the steps of:
 a) DNA isolation from the sample and from standards comprising DNA of said pathogens and/or beneficial microorganisms;
 b) amplification of the isolated DNAs of step a) by PCR;
 c) hybridization of the PCR products obtained on a Microarray-Chip as defined above;
 d) detection of the bound DNAs; and
 e) deduction therefrom if the sample contains pathogens and/or beneficial microorganisms.

The present invention also relates to a kit for the detection of pathogens and/or beneficial microorganisms in an organic sample comprising:

(i) the nucleic acids of the following sequences: SEQ No 1 SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, (ii) the nucleic acids of sequences having at least 80% identity with SEQ ID No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, or (iii) the nucleic acids of complementary sequences of (i) or (ii).

The present invention also relates to a method of treating a diseased turfgrass comprising the steps of:
a) detecting by a method combining PCR and Microarray-Chip the absence or the presence of nucleic acids from at least one pathogenic fungi and/or bacteria in a sample of soil in which the diseased turfgrass is growing, or in a sample of the diseased turfgrass, with at least one nucleic acid as defined above, in particular with the set of nucleic acids as defined above;
b) if nucleic acids from one or more pathogenic fungi and/or bacteria have been detected in step a), selecting one or more antifungal and/or antibacterial agents which target the one or more pathogenic fungi and/or bacteria from which nucleic acids have been detected; and
c) applying the selected one or more antifungal and/or antibacterial agents of step b) to the diseased turfgrass.

DETAILED DESCRIPTION OF THE INVENTION

Nucleic acids, as intended herein can be of any type, however it is preferred that they are DNA.

The table 1 below provides details on the nucleic acid sequences that can be used for the identification of the assigned species. It gives the reference SEQ ID, the name of the oligonucleotide, the corresponding species and which type of the 2 PCRs is needed to amplify them (ITS: genomic region comprising of genes and intergenic regions encoding the ribosomal RNA in fungi; 16S rRNA: genomic region encoding the 16S ribosomal RNA in bacteria).

TABLE 1

| SEQ ID No | Oligo ID | Species | Nucleic acid sequences | Region |
|---|---|---|---|---|
| 1 | ARME | Armillaria mellea | GGGTTGCTTGCTTGCGAGCTCC | ITS |
| 2 | ASPH | Ascochyta phleina | CTGGTGTTTGGACTCGCCTTAAAAC | ITS |
| 3 | BISO | Bipolaris sorokiniana | GCACATATTTTGCGCTTTGTATCAGG | ITS |
| 4 | BLGR | Blumeria graminis | TCCGCCAGGGAARACCAAAACTCT | ITS |
| 5 | CEZE | Cercospora zebrina | CGGAGCGCGGGCCGTCGCG | ITS |
| 6 | CLPU | Claviceps purpurea | ACTTATACCCAAAACGTTGCCTCG | ITS |
| 7 | COTR | Colletotrichum trifolii | CATTATCGAGTTTACGCTCCATAAC | ITS |
| 8 | COFU | Corticium fuciforme | GCGCAGCTATTAGATCTACGGTG | ITS |
| 9 | CUAF | Curvularia affinis | GCAAGGCTGGAGTATTTTATTACCCT | ITS |
| 10 | DRDI | Drechslera dictyoides | CCGTGGCCTTGTTGCCACGCCC | ITS |
| 11 | DRPH | Drechslera phlei | ATTGGGGCCTTGTTGCCACACCC | ITS |
| 12 | DRPO | Drechslera poae | TTTTGCGCTTTGTCCAGTTGCGG | ITS |
| 13 | DRSI | Drechslera siccans | GATTCGTCGCCCCCCCTCCTGG | ITS |
| 14 | DRTR | Drechslera tritici-repentis | GACCTTATTCAAACCTTTTTTTCAGTT | ITS |

TABLE 1-continued

| SEQ ID No | Oligo ID | Species | Nucleic acid sequences | Region |
|---|---|---|---|---|
| 15 | EPTY | *Epichloe typhina* | GCTGTTGGGGACCGGCTCACCCG | ITS |
| 16 | EXTU | *Exserohilum turcicum* | TGACCGTTGTCACGAGACGACTTTAT | ITS |
| 17 | FUCU | *Fusarium culmorum* | CTTGGTGTTGGGAGCTGCAGTCC | ITS |
| 18 | FUPO | *Fusarium poae* | CCATTGCGTAGTAGTAAAACCC | ITS |
| 19 | GAGR | *Gaeumannomyces graminis* | AACGCGCTTCGTICGGAGGCTT | ITS |
| 20 | FUPR | *Gibberella intermedia* | TTCAACCCTCAAGCCCCCGGGTTTG | ITS |
| 21 | GLCA | *Gliocladium catenulatum* | CGAAGTAGTGATATTCCGCATCGG | ITS |
| 22 | GLGR | *Glomerella graminicola* | GTTAGGGGGTCCCCTCTCCGG | ITS |
| 23 | KACA | *Kabatiella caulivora* | CTCGGTCTCGAGCCGCCGG | ITS |
| 24 | LEKO | *Leptosphaeria korrae* | ACACCCCATTGAACCTATTTATTTTYAA | ITS |
| 25 | LEAU | *Leptosphaerulina australis* | ACATCTCGCGCTTTGCATTCAGAA | ITS |
| 26 | MAPH | *Macrophomina phaseolina* | CGATTTTGGGGGTGGCTAGTGC | ITS |
| 27 | MAPO | *Magnaporthe poae* | CTCTGAGTACGAAAAGAACCTGAAA | ITS |
| 28 | MAOR | *Marasmius oreades* | TGCTGGCTCTTCTAGAGTCGGCTC | ITS |
| 29 | MIBO | *Microdochium bolleyi* | GGCCAGACGACAGCCATAAACC | ITS |
| 30 | MINI | *Microdochium nivale* | CGCCGGTGGACTACCTAAACTCT | ITS |
| 31 | MITR | *Microsphaera trifolii* | CGTCGTCGCTGTTCGCAAGGAC | ITS |
| 32 | MYRO | *Myrothecium roridum* | TCGGGCAACGGAACCAGGCGC | ITS |
| 33 | NESP | *Neotyphodium sp.* | GTTGCCTCGGCGGGCACGGC | ITS |
| 34 | OPHE | *Ophiosphaerella herpotricha* | CCAGTTATATAGGCACCCAATAAGCC | ITS |
| 35 | LENO | *Ophiosphaerella narmari* | CACCAAACCAGCTTGGGAAACCTT | ITS |
| 36 | PETR | *Peronospora trifoliorum* | GTCACGTGGTCTTGGTTTTGAA | ITS |
| 37 | PHSP | *Phyllachora vulgata* | CGCAACCGGGAGCCGCGGCGCGG | ITS |
| 38 | PLBR | *Phytophthora brassicae* | TGGACTGGCTTCGGCTAGACTGG | ITS |
| 39 | PHCA | *Phytophthora cactorum* | ACCATAGCTCAGTTGCTTGGCTTTT | ITS |
| 40 | PHCI | *Phytophthora citricola* | TGGCGAATGTTTGGACTTCGGTCT | ITS |

TABLE 1-continued

| SEQ ID No | Oligo ID | Species | Nucleic acid sequences | Region |
|---|---|---|---|---|
| 41 | PHDR | Phytophthora drechsleri | GCGCAAGCTGGGGTGGRCGAG | ITS |
| 42 | PHFR | Phytophthora fragariae | GAACTTGTGTCTCTGCGGCGCG | ITS |
| 43 | PHME | Phytophthora megasperma | AACTGGTGAACCGTAGCTGTGTGGT | ITS |
| 44 | PHNI | Phytophthora nicotianae | CCGTACATTAAACTTGACTTTCTTCC | ITS |
| 45 | PSME | Pseudopeziza medicaginis | GGAACTCCACCCTTGAATACACTG | ITS |
| 46 | PUCO1 | Puccinia coronata | CGACCCCTTTTATAATTCACCCAAC | ITS |
| 47 | PUCO2 | Puccinia coronata | CTAAAAAACCCCTCATAACCTTTTTTT | ITS |
| 48 | PUGRA | Puccinia graminis | CTCCTAAAACCCAATATCTTATTTTTAAG | ITS |
| 49 | PUPO | Puccinia poae-nemoralis | CAATACTGCCATCTTGTTTTTGAAGG | ITS |
| 50 | PUPA | Puccinia poarum | ATACTTGCCATCTTTTTGGAAGG | ITS |
| 51 | PURE | Puccinia recondita | CCTAAAAACCCCCCTTATCA | ITS |
| 52 | PUSO | Puccinia sorghi | CAACCTTTTTGGAGTATTCTAATGAT | ITS |
| 53 | PUST | Puccinia striiformis | ATACTGCCATCTTATTKAAGGGAGAC | ITS |
| 54 | PUTR | Puccinia triticina | CAGGGCTATCCCCCTGCCAGG | ITS |
| 55 | PYLY | Pyrenochaeta lycopersici | GGAGGGTTGCGCACTTTGTGCGTG | ITS |
| 56 | PYAP | Pythium aphanidermatuma | GACGCCCTGTTTTCGGATAGGG | ITS |
| 57 | PYDE | Pythium debaryanum | TGGCGTGCGTTTGCTTGCGCTTC | ITS |
| 58 | PHGR | Pythium graminicola | CTATACTCCGAGAACGAAAGTTTTTGG | ITS |
| 59 | PYIR | Pythium irregulare | TAGTAGTGTGTGTRGCACGTTGTC | ITS |
| 60 | PYMA | Pythium mastophorum | TGTTTTTGTTTTGTGGAAATACGCTGTTT | ITS |
| 61 | PYSU | Pythium sulcatum | GTAGAATTTTGCTGCTCTTGGGCG | ITS |
| 62 | PYUL | Pythium ultimum | CTGTGTAGTCAGGGATGGAATGTGC | ITS |
| 63 | RACO | Ramularia collo-cygni | TGAACGCATCATGTTGCTTCGGG | ITS |
| 64 | RHCE | Rhizoctonia cerealis | CTGGCTTTTGTTTTGGATTTGGAGGT | ITS |
| 65 | RHFR | Rhizoctonia fragariae | CAGCGACAACCGACTCTAAGTTCA | ITS |
| 66 | RHOR | Rhynchosporium orthosporum | CTCGTGAAACACATGAAGTCTGAG | ITS |
| 67 | RHSE | Rhynchosporium secalis | TCGGCGCCCCAGGAGAAATCCT | ITS |
| 68 | SCBO | Sclerotinia borealis | AGTCCATGTCCGCAATGGCAGG | ITS |
| 69 | SCHO | Sclerotinia homoeocarpa | AACACATACCTCTCGTTACAGGGTC | ITS |

TABLE 1-continued

| SEQ ID No | Oligo ID | Species | Nucleic acid sequences | Region |
|---|---|---|---|---|
| 70 | SCSC | Sclerotinia sclerotiorum | GAGCTGCTCTTCGGGGCCTTGTAT | ITS |
| 71 | SCTR | Sclerotinia trifoliorum | CTTGTATGCGCGCCAGAGAATATCA | ITS |
| 72 | SEMA | Septoria macropoda | TATTGGGCGTCCGCGGGGGA | ITS |
| 73 | SETR | Septoria tritici | GCGGAGTTCACGAGCCCTCAC | ITS |
| 74 | STSA | Stemphylium sarcinaeforme | GCGCCTTGTCTCTCGCGAGAC | ITS |
| 75 | THCU | Thanatephorus cucumeris | AGCTGGATCTCAGTGTTATGCTTGG | ITS |
| 76 | CHEL | Thielaviopsis basicola | GTGCCTCTCGGGGCTTCTGCCG | ITS |
| 77 | CHTH | Thielaviopsis populi | CCTGTGTAGTAATGCTTAGCTTACAC | ITS |
| 78 | TICA | Tilletia caries | CTACGGAGGGGTGGCTGCGTTG | ITS |
| 79 | TICO | Tilletia controversa | CTACGGAGGGGTGGCTGCGTTG | ITS |
| 80 | TRHA | Trichoderma hamatum | ACAGCTCTGAGCAAAAATTCAAAATG | ITS |
| 81 | TYIN | Typhula incarnate | GTCCAATGTAGGCGCAGCGTAA | ITS |
| 82 | TYIS1 | Typhula ishikariensis | ATTAGCTGGAACCTCTTGTGGACC | ITS |
| 83 | TYIS2 | Typhula ishikariensis | ATTAGCTGGAACCTCTTGTGGACC | ITS |
| 84 | URDA | Uromyces dactylidis | CTCATTAAACAATTTTTTCTTATAAAGATTG | ITS |
| 85 | URTR | Uromyces trifolii-repentis | GTCATTGCACTCAGGTAGACGTAACA | ITS |
| 86 | USMA | Ustilago maydis | CTTTTTTCTTTTGGAAAAGGTTGACG | ITS |
| 87 | USNU | Ustilago nuda | ACAGACAATTTTATTGAACACTTTTT | ITS |
| 88 | USST | Ustilago striiformis | TTTGAAGAGTTGGCGGATCGGTAT | ITS |
| 89 | USTR | Ustilago tritici | ACGGACAATTTTATTTAACACTTTTG | ITS |
| 90 | VEDA | Verticillium dahliae | GCCCTTAAAAKCAGTGGCGGACC | ITS |
| 91 | BASU | Bacillus amyloliquefaciens | TAATACATGCAAGTCGAGCGGACAGAT | 16S rRNA |
| 92 | PSCH | Pseudomonas chlororaphis | GGGTACTTACCTAATACGTGAGTAT | 16S rRNA |
| 93 | SEEN | Serratia entomophila | GAAGGGTARTGTCTTAATACGGCATT | 16S rRNA |
| 94 | SEPL | Serratia plymuthica | GGAAGGGYAGTGTGTTAATAGCAC | 16S rRNA |
| 95 | STAL | Streptomyces albidoflavus | ATGACTGTCCATCGCATGGTGGAT | 16S rRNA |
| 96 | STGR1 | Streptomyces graminofaciens | CTGCGGATCGCATGGTCTGCG | 16S rRNA |
| 97 | STGR2 | Streptomyces griseoviridis | AATACTTCTCCTCGCATGGGGAGG | 16S rRNA |

TABLE 1-continued

| SEQ ID No | Oligo ID | Species | Nucleic acid sequences | Region |
|---|---|---|---|---|
| 98 | STRI | Streptomyces rimosus | ATGACACACGACCGCATGGTCTGT | 16S rRNA |
| 99 | STSC | Streptomyces scabiei | CACCGGAAACGGCCAGAGATGGTCG | 16S rRNA |
| 100 | XATR | Xanthomonas translucens | GAGTGTGGTAGAGGATGGCGGAA | 16S rRNA |

Nucleotide sequences are written using the nucleotide base code (IUPAC) (Cornish-Bowden, A. Nucl Acid Res 13, 3021-3030 (1985)). In nucleotide sequences letters G, A, T, C stand for Guanine, Adenine, Thymine and Cytosine, M stands for A and C, R stands for A and G, W stands for A and T, Y stands for C and T, S stands for C and G, K stands for G and T, H stands for A and C and T, V stands for A and C and G, D stands for A and G and T, B stands for C and G and T, N stands for A and C and G and T.

As intended herein, the nucleic acids comprising or consisting of sequences having at least 80% identity with SEQ ID No 1 to 100, as previously mentioned, are nucleic acid sequences 80 to 100% identical to the nucleic acid sequences of SEQ ID No 1 to 100. In particular, these nucleic acid sequences are 90 to 100% identical, more particularly 95 to 100%, most preferably 95, 96, 97, 98, 99 or 100% identical to the nucleic acid sequences of SEQ ID No 1 to 100.

By nucleic acids having at least, for example, 95% identity with a query nucleic acid sequence of the present invention, it is intended that the nucleic acid sequence is identical to the query sequence except that the sequence may include up to five nucleic acid alterations per each 100 nucleic acids of the query nucleic acid sequence. In other words, to obtain a nucleic acid having a sequence at least 95% identical to a query nucleic acid sequence, up to 5% (5 of 100) of the nucleic acids in the subject sequence may be inserted, deleted, or substituted with another nucleic acid.

In the context of the present application, the percentage of identity is calculated using a global alignment (i.e. the two sequences are compared over their entire length).

Methods for comparing the identity of two or more sequences are well known in the art. The <<needle>> program, which uses the Needleman-Wunsch global alignment algorithm (Needleman and Wunsch, 1970 J. Mol. Biol. 48:443-453) to find the optimum alignment (including gaps) of two sequences when considering their entire length, may for example be used.

In particular, the maximum length of the nucleic acids according to the invention is less than or equal to 500 nucleotides, preferably less than or equal to 300, more preferably less than or equal to 200, still more preferably less than or equal to 100, even more preferably less than or equal to 50, most preferably less than or equal to 35; in a particular embodiment the nucleotide sequence length is from 19 to 31 nucleotides.

In the context of the invention, by "at least one nucleic acid", it is meant, for example, 1, 2, 3, 10, 20, 30, 40, 50 or more (up to 100) nucleic acids comprising or consisting of sequences chosen from the sequences SEQ No 1 to 100, sequences at least 80% identical to SEQ ID No 1 to 100 and complementary sequences thereof. It can for example be at least 40 nucleic acids, at least 50, 60, 70, 80 or 90 nucleic acids comprising or consisting of sequences chosen from said sequences. It has to be noted that any of the sequences above mentioned in (i), (ii) and (iii) can be chosen and combined together.

In a particular embodiment of the uses, methods and Microarray-Chips according to the invention, at least 40 nucleic acids, and more particularly at least 50 nucleic acids are used.

"Stringent conditions" can be easily defined by the person skilled in the art using common knowledge. If necessary, guidance for defining such conditions can be found in numerous textbooks, such as Tijssen, 1993, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. In particular, stringent conditions according to the invention can be constituted using a hybridization reaction requiring an optimized combination of hybridization buffer and hybridization temperature, depending on the ingredients of the hybridization buffer. Such determination of hybridization conditions falls within the routine work of the person skilled in the art.

By way of example, which has not to be considered as limiting the present invention, hybridization can be carried out at 55° C. according to the ALERE DNA Array protocol and by using the hybridization buffers mentioned therein (Hybridisation Kit, ALERE Technologies GmbH. Germany, order numbers 245200100 and 24520K100).

As intended herein, "one pathogen" is a microorganism of any type that causes disease in its host. The host may be an animal, a plant, or even another microorganism. In particular, the pathogen is selected from bacteria and/or fungi. More particularly, fungi and/or bacteria are selected from the group consisting of: *Armillaria mellea, Ascochyta phleina, Bipolaris sorokiniana, Blumeria graminis, Cercospora zebrine, Claviceps purpurea, Colletotrichum trifolii, Corticium fuciforme, Curvularia affinis, Drechslera dictyoides, Drechslera phlei, Drechslera poae, Drechslera siccans, Drechslera tritici-repentis, Epichloe typhina, Exserohilum turcicum, Fusarium culmorum, Fusarium poae, Gaeumannomyces graminis, Gibberella intermedia, Gliocladium catenulatum, Glomerella graminicola, Kabatiella caulivora, Leptosphaeria korrae, Leptosphaerulina australis, Macrophomina phaseolina, Magnaporthe poae, Marasmius oreades, Microdochium bolleyi, Microdochium nivale, Microsphaera trifolli, Myrothecium roridum, Neotyphodium sp., Ophiosphaerella herpotricha, Ophiosphaerella narmari, Peronospora trifoliorum, Phyllachora vulgata, Phytophthora brassicae, Phytophthora cactorum, Phytophthora citricola, Phytophthora drechsleri, Phytophthora fragariae, Phytophthora megasperma, Phytophthora nicotianae, Pseudopeziza medicaginis, Puccinia coronata, Puccinia coronate, Puccinia graminis, Puccinia poae-nemoralis, Puccinia*

*poarum, Puccinia recondite, Puccinia sorghi, Puccinia striiformis, Puccinia triticina, Pyrenochaeta lycopersici, Pythium aphanidermatuma, Pythium debaryanum, Pythium graminicola, Pythium irregulare, Pythium mastophorum, Pythium sulcatum, Pythium ultimum, Ramularia collocygni, Rhizoctonia cerealis, Rhizoctonia fragariae, Rhynchosporium orthosporum, Rhynchosporium secalis, Sclerotinia borealis, Scierotinia homoeocarpa, Sclerotinia sclerotiorum, Sclerotinia trifoliorum, Septoria macropoda, Septoria tritici, Stemphylium sarcinaeforme, Thanatephorus cucumeris, Thielaviopsis basicola, Thielaviopsis populi, Tilletia caries, Tilletia controversa, Trichoderma hamatum, Typhula incarnate, Typhula ishikariensis, Typhula ishikariensis, Uromyces dactylidis, Uromyces trifolii-repentis, Ustilago maydis, Ustilago nuda, Ustiago striiformis, Ustilago tritici, Verticillium dahliae; Bacillus amyloliquefaciens, Pseudomonas chlororaphis, Serratia entomophila, Serratia plymuthica, Streptomyces albidoflavus, Streptomyces graminofaciens, Streptomyces griseoviridis, Streptomyces rimosus, Streptomyces scabiei, Xanthomonas translucens.*

It has to be understood that a fungus and/or bacterium being part of the above mentioned list but which could have synonymous names and/or which could have been renamed, are also included. In addition, closely related species of those mentioned in the above list are also in the frame of the present invention. By closely related species, it is meant species having an identical sequence to one or more nucleotide(s) of SEQ ID NOs 1 to 100, as described above, within their conserved regions.

In a particular embodiment, the present invention relates to the use of a set of nucleic acids comprising or consisting of:

(i) the sequences SEQ No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, (ii) the sequences comprising or consisting of sequences having at least 80% identity with SEQ No 1, SEQ ID No 2, SEQ ID No 3, SEQ ID No 4, SEQ ID No 5, SEQ ID No 6, SEQ ID No 7, SEQ ID No 8, SEQ ID No 9, SEQ ID No 10, SEQ ID No 11, SEQ ID No 12, SEQ ID No 13, SEQ ID No 14, SEQ ID No 15, SEQ ID No 16, SEQ ID No 17, SEQ ID No 18, SEQ ID No 19, SEQ ID No 20, SEQ ID No 21, SEQ ID No 22, SEQ ID No 23, SEQ ID No 24, SEQ ID No 25, SEQ ID No 26, SEQ ID No 27, SEQ ID No 28, SEQ ID No 29, SEQ ID No 30, SEQ ID No 31, SEQ ID No 32, SEQ ID No 33, SEQ ID No 34, SEQ ID No 35, SEQ ID No 36, SEQ ID No 37, SEQ ID No 38, SEQ ID No 39, SEQ ID No 40, SEQ ID No 41, SEQ ID No 42, SEQ ID No 43, SEQ ID No 44, SEQ ID No 45, SEQ ID No 46, SEQ ID No 47, SEQ ID No 48, SEQ ID No 49, SEQ ID No 50, SEQ ID No 51, SEQ ID No 52, SEQ ID No 53, SEQ ID No 54, SEQ ID No 55, SEQ ID No 56, SEQ ID No 57, SEQ ID No 58, SEQ ID No 59, SEQ ID No 60, SEQ ID No 61, SEQ ID No 62, SEQ ID No 63, SEQ ID No 64, SEQ ID No 65, SEQ ID No 66, SEQ ID No 67, SEQ ID No 68, SEQ ID No 69, SEQ ID No 70, SEQ ID No 71, SEQ ID No 72, SEQ ID No 73, SEQ ID No 74, SEQ ID No 75, SEQ ID No 76, SEQ ID No 77, SEQ ID No 78, SEQ ID No 79, SEQ ID No 80, SEQ ID No 81, SEQ ID No 82, SEQ ID No 83, SEQ ID No 84, SEQ ID No 85, SEQ ID No 86, SEQ ID No 87, SEQ ID No 88, SEQ ID No 89, SEQ ID No 90, SEQ ID No 91, SEQ ID No 92, SEQ ID No 93, SEQ ID No 94, SEQ ID No 95, SEQ ID No 96, SEQ ID No 97, SEQ ID No 98, SEQ ID No 99 and SEQ ID No 100, or (iv) the complementary sequences of (i) or (ii), for the detection of all of the fungus and bacteria mentioned in the above list.

As intended herein, "one beneficial microorganism" is any organism that benefits the growing process, including insects, arachnids, other animals, plants, bacteria, fungi, viri, and nematodes. In particular, the beneficial microorganism is a plant growth promoting rhizobacteria.

As intended herein, the sample in which nucleic acids are to be detected can be of any type of organic substrate liable to contain nucleic acids. In particular, it can be a turfgrass, soil, natural fertilizer, seed or crop sample. More particularly, the natural fertilizer can be of animal origin such as animal dung or animal manure, or of plant or herbal origin such as leaves, stalk, root, seed, fruit body or blossom.

Where the sample is a turfgrass sample, it can be a sample obtained from the turf grass as a whole or from a sample of a part of the turfgrass, such as the root, seeds or soil. In particular, the sample can be a turfgrass root or seed or a blade of the turfgrass sample.

In particular, turfgrasses to be considered within the frame of the present invention are notably described in the Compendium of Turfgrass Diseases, Third Edition (2005) issued by the American Phytopathological Society.

More particularly, the turfgrass sample is selected from the group consisting of the Festaceae, Aveneae, Triticeae, Chlorideae, Zoysieae, Paniceae and Andropogoneae Tribe.

Where the sample is a soil sample, it is preferably taken directly under the diseased area or in the vicinity of the diseased area, preferably turfgrass.

The sample can be obtained directly from turfgrass, fertilizer, seed, crop or soil, or be obtained after treatment steps, such as grinding, freezing or extraction, in particular nucleic acid extraction, steps.

In a particular embodiment, the sample in which nucleic acids are to be detected is not of human origin.

As intended in the present invention, the at least one nucleic acid as defined above or the set of nucleic acid as defined above is to be used in an hybridization technique, in particular a nucleic acid hybridization-based detection method. Examples of such methods are Microarray-Chip, Southern blot analysis, Northern blot analysis, or Polymerase chain reactions (PCR) wherein the nucleic acids can be used as a primer, probe or template for hybridization. Depending on the method of choice, the nucleic acid is labeled or unlabeled. Examples of such labels are biotin, streptavidin, fluorescent chemicals, radioactive isotopes, Digoxigenin and many others which allow for the detection of bound DNA.

Nucleic acid hybridization-based detection methods are well known to a person skilled in the art.

Microarray-Chips, for instance, are well described in "Microarray Technology in Practice" by Steve Russell (2008, ISBN-10: 012372516X, ISBN-13: 978-0123725165) and are used in numerous publications (Oh S, et al., Genomic diversity of *Escherichia* isolates from diverse habitats. PLoS One. 2012; 7(10):e47005.doi: 10.1371/journal.pone.0047005. Epub 2012 Oct. 8).

Polymerase chain reaction (PCR), Southern blot analysis and Northern blot analysis, for instance, are well described in Molecular Cloning: A Laboratory Manual, 4$^{th}$ Edition (2012, ISBN-10: 1936113422|ISBN-13: 978-1936113422).

For polymerase chain reactions as detection method of choice, at least one nucleic acid as defined above or the set of nucleic acid as defined above, is used to convey specificity of the PCR, wherein the nucleic acid can be labeled or unlabeled and be used as primer or probe.

For Southern or Northern blot analysis as detection method of choice, at least one nucleic acid as defined above or the set of nucleic acid as defined above is used during hybridization wherein the nucleic acid can be labeled or unlabeled.

For Microarray-Chip as detection method of choice, at least one nucleic acid as defined above or the set of nucleic acid as defined above is used as probe on the Microarray-Chip, wherein the nucleic acid can be labeled or unlabeled.

The Microarray-Chip hybridization methods above can be combined with general PCRs to increase sensitivity or specificity of the assay. At least one nucleic acid sequence as defined above or the set of nucleic acid as defined above will be part of the final PCR product. Such amplification methods, using PCRs, and variations thereof, are well known to the person skilled in the art.

In a particular embodiment of the present invention, the hybridization technique can thus comprise a PCR combined with a Microarray-Chip, wherein the PCR increased the sensitivity, reduces background and/or adds detection label to the PCR product.

If nucleotide sequences from fungi or isolated DNA from fungi are to be amplified by PCR, the PCR comprises primers targeting a sequence within the genome (Internal Transcribed Spacer (ITS)) of the one or more fungi comprising at least one nucleic acid sequence described above. In particular, one primer targets the 18S rDNA/ITS1 region or the ITS2/28S rDNA region of the one or more fungi. The fungal rRNA operon comprises the 18S rRNA gene, the Internal Transcribed Spacer 1 (ITS1), the 5.8S rRNA gene, the Internal Transcribed Spacer 2 (ITS2), and the 28S rRNA gene. The 18S rDNA/ITS1 and ITS2/28S rDNA regions thus relate to the regions of the genome of the one or more fungi in the vicinity respectively of the junction of the 18S rRNA gene and ITS1, and of the junction of ITS2 and the 28S rRNA gene. As will be clear to anyone of skill in the art, to design one nucleic acid as a forward primer, the primer which targets the 18S rDNA/ITS1 region or the ITS2/28S rDNA region will be a reverse primer, and vice versa. The sequences of the 18S rDNA/ITS1 and ITS2/28S rDNA regions are well known to one of skill in the art and can usually be accessed from public sequence databases. Where sequences of the 18S rDNA/ITS1 and ITS2/28S rDNA regions would not be publicly available for a particular fungus species, they can be routinely sequenced. Besides, it is well within the common knowledge of anyone skilled in the art to select primers within the known sequences.

By way of example of a primer targeting the 18S rDNA/ITS1 region, one can cite the so-called "ITS1 primer" of sequence TCCGTAGGTGAACCTGCGG (SEQ ID No 101). Conversely, by way of example of a primer targeting the ITS2/28S rDNA region one can cite the so-called "ITS4 primer" of sequence TCCTCCGCTTATTGATATGC (SEQ ID No 102). Still other examples are available from WO 2009/147017 A1, White et al. 1990, Gardes & Bruns 1993.

If nucleotide sequences from bacteria or isolated DNA from bacteria are to be amplified by PCR, the PCR comprises primers targeting a sequence within the genome (16S rRNA) of the one or more bacteria comprising at least one nucleic acid sequence described above. However, it is preferred that the primer targets the gene for the 16S rRNA. As will be clear to anyone skilled in the art, to design one nucleic acid as a forward primer, the other primer will be a reverse primer, and vice versa. The sequences of the 16S rRNA gene are well known to one skilled in the art and can usually be accessed from public sequence databases. Where sequences of the 16S rRNA gene would not be publicly available for a particular bacterial species, they can be routinely sequenced. Besides, it is well within the common knowledge of anyone skilled in the art to select primers within the known sequences.

By way of example of a primer targeting the 16S rRNA, one can cite the so-called "EUB8m_f primer" of sequence AGAGTTTGATCMTGGCTCAG (SEQ ID No 103) and "EUB1088_r primer" of sequence CTCGTTGCGGGACTTAACC (SEQ ID No 104), wherein one primer acts as forward primer and the other as reverse primer.

As intended herein the primers to be used may be unmodified or modified nucleic acids, in particular DNA. Where the primers are modified nucleic acids they can notably be labeled nucleic acids, in particular biotin labeled, fluorescently labeled or radioactively labeled nucleic acids.

Nucleic acids may need to be isolated and purified from organic samples (e.g. turfgrass, soil, crops, plants, fertilizers, seeds etc.). Methods for the isolation of nucleic acids are well known for the person skilled in the art and may depend on the method for detection used for detection and source of organic sample. By way of example, methods for nucleic acid isolation are described in the scientific literature (e.g. Michele K. Nishiguchi, Phaedra Doukakis, Mary Egan et al., "DNA Isolation Methods", Methods and Tools in Biosciences and Medicine, Techniques in molecular systematics and evolution, ed. by Rob DeSalle et al.© 2002 Birkhauser Verlag Basel/Switzerland). Still other examples are many commercially available methods or kits (e.g. "DNeasy® Plant Mini Kit (QIAGEN 69104) or "PowerSoil® DNA Isolation Kit (MO BIO laboratories Inc, Cat no. 12888-100).

As mentioned above, the present invention also relates to a Microarray-Chip comprising at least one nucleic acid according to the present invention.

In particular, the Microarray-Chip comprises the all set of nucleic acids according to the invention, and mentioned above.

According to an embodiment of the present invention, the Microarray-Chip according to the invention is used for the detection of at least one pathogen and/or beneficial microorganism in a sample, the said pathogen, beneficial microorganism and sample being as defined above.

In particular, the Microarray-Chip according to the invention is used for the detection of all of the fungi and bacteria mentioned in the above list.

As mentioned above, the present invention also relates to a detection method of pathogens and/or beneficial microorganisms in an organic sample.

In particular, this method is for detection of all of the fungi and bacteria defined in the above mentioned list, and two PCRs are conducted in its step b), the first directed to fungus DNAs and the second directed to bacterial DNAs.

In a particular embodiment, the two PCRs are combined into one single reaction tube.

Experimental Procedure

DNA is isolated from organic sample (e.g. turfgrass, soil, crops, plant parts etc.) and from standards (isolated bacteria, isolated fungus etc.). Methods are known for a skilled person. Examples are described in the scientific literature (e.g. Michele K. Nishiguchi, Phaedra Doukakis, Mary Egan et al., "DNA Isolation Methods", Methods and Tools in Biosciences and Medicine, Techniques in molecular systematics and evolution, ed. by Rob DeSalle et al.© 2002 Birkhäuser Verlag Basel/Switzerland) and many commercially methods are available, too. (e.g. "DNeasy® Plant Mini Kit (QIAGEN 69104) or "PowerSoil® DNA Isolation Kit (MO BIO laboratories Inc, Cat no. 12888-100).

A Fungi-PCR (ITS) can be conducted. By means of a fungi specific, but species unspecific PCR, the rDNA internal transcribed spacer sequence (ITS) is amplified. Example for such a primer pair are the ITS1 (TCCGTAGGTGAAC-CTGCGG) (SEQ ID No 101) and ITS4 (TCCTCCGCTT-ATTGATATGC) (SEQ ID No 102), targeting the 18S rDNA/ITS1 and ITS2/28S rDNA region, as described elsewhere (White et al. 1990, Gardes & Bruns 1993). Other primer pairs, amplifying the same region, are applicable, too, with this method. A person skilled in the art will be able to design and/or use such primers that target this region in all organisms.

A Bacterial-PCR (16S rRNA) can also be conducted. By means of a bacterial specific, but species unspecific PCR, the bacterial 16S rDNA is amplified. Example for such a primer pair is "EUB8m_f primer" of sequence AGAGTTTGATC-MTGGCTCAG (SEQ ID No 103) and "EUB1088_r primer" of sequence CTCGTTGCGGGACTTAACC (SEQ ID No 104). Other primer pairs, amplifying the same region or the whole 16S rRNA, are applicable, too, with this method. A person skilled in the art will be able to design and/or use such primers that target this region in all organisms.

The two PCRs can be combined into a single reaction tube. The person skilled in the art will be able to do this.

Eventually the PCR product has to be labelled. Many methods and dyes exist to do so (fluorescent dye, biotin, isotopes, Digoxigenin labelling). The PCR product can be labelled during PCR (e.g. labelled primers) or the PCR product is labelled after amplification.

The PCR product is purified by means of standard methods (e.g. QIAGEN PCR purification Kit).

The Individual or combined purified PCR products are hybridized to the DNA on a Microarray-Chip according to the present invention and as described above, and stringently washed in order to remove unbound DNA (e.g. Hybridisation Kit, ALERE Technologies GmbH, Germany, order numbers 245200100 and 24520K100).

Bound DNA is detected by a detection method specific to the label that was added to the PCR product during amplification.

Such detection methods are well known by the person skilled in the art. For example, fluorescent labels can be measured using apparatus capable to excite the fluorochrom and to measure the emitted signal using fluorescent sensitive cameras. Biotin labels can be detected using Streptavidin linked with horseradish peroxidase (HRP). HRP catalyzes the conversion substrates into coloured products. The presence of HRP and thus of biotin is then measured by the detection of processed substrate. Examples of substrates are 3,3'-Diaminobenzidine or 3,3',5,5'-Tetramethylbenzidine. Methods for product measurement depend on the substrate and may be chemiluminescent signals sensitive cameras or optical cameras measuring the optical spectrum, including the human eye. Specific examples of such apparatus are ATR3 ArrayTube™ Reader (for Microarrays, by Identibac, Alere) or ChemiDoc™ MP imager (for southern and northern blots by Biorad) and Rotor Gene Q (for PCR by QIAGEN).

It is then possible to deduce therefrom if the sample contains pathogens and/or beneficial microrganisms and to identify the species present in the sample.

In particular, this method can be used for screening of organic samples before its use for absence of pathogens and can detect pathogens already before the pathogen emerges and causes disease.

As mentioned above, the present invention also relates to a detection kit for the detection of pathogens and/or beneficial microorganisms in an organic sample.

As mentioned above, the present invention also relates to a method of treating a diseased turfgrass.

Thereby, thanks to the present invention, analysis of turfgrass, soils, natural fertilizers (e.g. absence of pathogens), seeds, and crops and detection of causative pathogen in grass showing the disease is possible.

The invention will be further illustrated by the following example.

Example 1

Microarray tubes were covalently linked with nucleic acid sequences according to the invention (SEQ ID NOs 1 to 100) (provided by Alere Technologies GmbH, Jena, Germany). The nucleic acid sequences according to the invention and above described were spotted in duplicates onto the microarray in order to generate a reproducible result. Each spot contained 0.02 µmol of nucleotide and the nucleotides were immobilized onto the array by a 3'C7-amino modification.

DNA from isolated fungi, turfgrass or soil was extracted using the commercial kit PowerSoil® DNA Isolation Kit (from MO BIO laboratories Inc., order number 12888-100) according to the manufacturer's instructions. DNA from samples consisting of turfgrass was isolated using maximal 0.3 g of soil.

Amplification of fungal rDNA genomic region (ITS) was performed using the primer pairs ITS1 and ITS4 that contained a biotin label at their 5' end. Primers were purchased from Microsynth (Balgach, Switzerland). PCR products were purified using the "PCR purification kit" from Qiagen (#28104) to remove residual primers, buffer and nucleotides.

The resulting purified biotinylated PCR products were hybridized to the microarray tubes. The Hybridization protocol and reagents were from Alere (Hybridisation Kit, ALERE Technologies GmbH, Germany, order numbers 245200100). The hybridization temperature was increased (from 55 to 61° C.) to increase specificity. After hybridization and washing off unbound DNA, bound, biotinylated PCR products were detected using horseradish peroxidase labeled streptavidin and horseradish peroxidase substrate from Alere (Hybridisation Kit, ALERE Technologies GmbH, Germany, order numbers 24520K100).

The signal intensities on the microarray tubes and location to the spotted chip were measured with the ATR3 (Alere tube reader version 3). Intensity measurements produced a semi-quantitative value of the bound PCR-product. The analysis software (IconoClust, Standard version, Build: 3.6r0), developed by Alere, processed signal intensities and background signals received from a given spot and allocated signal intensities to the nucleic acid present at a given spot. Each spot produced signal intensities between approximately 0 and +1 (Arbitrary units), calculated from control spots and signal intensity. Results are provided in Table 2 below.

TABLE 2

Signal intensities detected in different samples (A-E: individual turfgrass samples. F: mix of isolated fungal cultures: *Bipolaris sorokiniana* strain 583, *Sclerotinia minor* strain 454, *Pyrenochaeta lycopersici* strain 45, expected to bind to probes BISO, SCSC and PYLY. *S.minor* is very closely related to *S.sclerotiorum* and expected to bind the probe. Signal intensities >0.07 are written in bold. Correspondence between Oligo ID and species can be found in Table 1.

| Oligo ID | A | B | C | D | E | F |
|---|---|---|---|---|---|---|
| ARME | 0.00 | −0.01 | 0.01 | 0.00 | 0.00 | 0.00 |
| ASPH | 0.65 | 0.84 | 0.28 | 0.35 | 0.62 | 0.06 |
| BASU | 0.05 | 0.01 | 0.00 | −0.01 | 0.00 | −0.01 |
| BISO | 0.00 | 0.00 | 0.00 | −0.01 | 0.12 | 0.83 |
| BLGR | 0.01 | 0.00 | 0.00 | 0.06 | 0.00 | 0.00 |
| CEZE | 0.00 | 0.00 | 0.00 | −0.01 | 0.01 | 0.00 |
| CHEL | 0.00 | 0.00 | −0.01 | 0.01 | −0.01 | −0.01 |
| CHTH | 0.00 | 0.01 | 0.01 | 0.01 | 0.01 | 0.01 |
| CLPU | 0.00 | 0.01 | 0.00 | 0.01 | 0.00 | 0.00 |
| COFU | 0.00 | 0.01 | 0.01 | 0.00 | 0.00 | 0.00 |
| COTR | 0.00 | 0.00 | 0.00 | 0.01 | 0.00 | 0.00 |
| CUAF | 0.00 | 0.00 | 0.00 | 0.18 | 0.00 | 0.00 |
| DRDI | 0.02 | −0.01 | −0.01 | 0.01 | −0.01 | 0.00 |
| DRPH | 0.00 | 0.00 | 0.01 | −0.01 | 0.00 | 0.00 |
| DRPO | 0.00 | 0.01 | 0.00 | −0.01 | −0.01 | 0.01 |
| DRSI | 0.00 | 0.01 | −0.01 | −0.01 | 0.00 | 0.00 |
| DRTR | 0.00 | 0.02 | 0.00 | −0.01 | −0.01 | 0.00 |
| EPTY | 0.00 | 0.00 | 0.01 | 0.00 | 0.00 | 0.01 |
| EXTU | 0.00 | 0.01 | 0.01 | 0.01 | −0.01 | 0.00 |
| FUCU | 0.00 | 0.01 | 0.00 | 0.00 | 0.00 | −0.01 |
| FUPO | 0.01 | 0.00 | −0.01 | −0.01 | 0.01 | 0.00 |
| FUPR | 0.01 | 0.86 | 0.60 | 0.79 | 0.24 | 0.01 |
| GAGR | 0.00 | 0.00 | 0.00 | 0.01 | 0.00 | 0.00 |
| GLCA | 0.01 | 0.01 | 0.00 | 0.02 | 0.01 | 0.00 |
| GLGR | −0.01 | −0.01 | −0.01 | −0.01 | 0.00 | 0.00 |
| KACA | 0.00 | 0.00 | 0.00 | 0.00 | 0.00 | −0.01 |
| LEAU | 0.03 | 0.81 | 0.04 | 0.05 | 0.22 | 0.00 |
| LEKO | −0.01 | 0.01 | 0.01 | 0.00 | 0.00 | 0.00 |
| LENO | 0.00 | 0.00 | 0.01 | 0.01 | −0.01 | −0.01 |
| MAOR | 0.00 | 0.00 | −0.01 | 0.00 | 0.00 | −0.01 |
| MAPH | 0.01 | 0.00 | 0.00 | −0.01 | 0.01 | 0.01 |
| MAPO | 0.00 | 0.01 | 0.00 | 0.00 | 0.00 | 0.00 |
| MBO | 0.00 | 0.05 | 0.00 | −0.01 | 0.00 | −0.01 |
| MINI | 0.53 | 0.01 | −0.01 | −0.01 | 0.00 | 0.00 |
| MITR | 0.01 | 0.01 | 0.00 | 0.00 | 0.01 | 0.00 |
| MYRO | 0.00 | 0.00 | 0.01 | −0.01 | 0.01 | 0.00 |
| NESP | 0.00 | 0.01 | 0.00 | 0.00 | 0.00 | 0.00 |
| OPHE | 0.00 | 0.00 | 0.00 | −0.01 | 0.00 | 0.00 |
| PETR | 0.00 | 0.01 | 0.00 | −0.01 | 0.00 | 0.00 |
| PHCA | 0.00 | 0.01 | −0.01 | 0.01 | 0.00 | 0.00 |
| PHCI | −0.01 | 0.01 | 0.00 | 0.01 | 0.01 | 0.00 |
| PHDR | −0.01 | 0.00 | −0.01 | 0.02 | 0.00 | 0.00 |
| PHFR | 0.00 | −0.01 | 0.00 | −0.01 | −0.01 | −0.01 |
| PHGR | 0.00 | 0.38 | 0.01 | 0.00 | −0.01 | −0.01 |
| PHME | 0.07 | −0.01 | 0.00 | 0.00 | 0.00 | 0.00 |
| PHNI | 0.00 | 0.00 | 0.00 | 0.01 | 0.00 | 0.00 |
| PHSP | 0.00 | 0.01 | 0.00 | −0.01 | 0.00 | 0.00 |
| PLBR | 0.01 | 0.00 | 0.00 | 0.02 | 0.00 | −0.01 |
| PSCH | 0.01 | 0.00 | −0.01 | 0.01 | −0.01 | −0.01 |
| PSME | 0.00 | 0.00 | 0.01 | 0.01 | 0.01 | 0.00 |
| PUCO1 | 0.00 | 0.01 | 0.00 | 0.00 | 0.01 | 0.00 |
| PUCO2 | 0.00 | 0.01 | 0.00 | −0.01 | 0.00 | 0.00 |
| PUGRA | −0.01 | 0.01 | 0.00 | 0.00 | 0.00 | 0.00 |
| PUPA | −0.01 | 0.01 | −0.01 | 0.00 | −0.01 | 0.00 |
| PUPO | 0.00 | 0.01 | 0.00 | −0.01 | 0.00 | 0.00 |
| PURE | −0.01 | 0.01 | 0.01 | 0.00 | 0.00 | 0.00 |
| PUSO | 0.00 | 0.01 | 0.01 | −0.01 | 0.01 | 0.00 |
| PUST | 0.00 | 0.01 | 0.01 | 0.01 | −0.01 | 0.00 |
| PUTR | 0.00 | 0.00 | 0.00 | 0.00 | 0.00 | 0.00 |
| PYAP | 0.00 | 0.00 | 0.01 | 0.01 | 0.01 | 0.00 |
| PYDE | 0.01 | 0.01 | 0.01 | 0.01 | −0.01 | 0.00 |
| PYIR | 0.00 | 0.00 | 0.01 | 0.00 | 0.00 | 0.01 |
| PYLY | 0.00 | 0.01 | 0.01 | 0.01 | 0.01 | 0.07 |
| PYMA | 0.01 | 0.00 | 0.01 | 0.00 | 0.00 | 0.00 |

TABLE 2-continued

Signal intensities detected in different samples (A-E: individual turfgrass samples. F: mix of isolated fungal cultures: *Bipolaris sorokiniana* strain 583, *Sclerotinia minor* strain 454, *Pyrenochaeta lycopersici* strain 45, expected to bind to probes BISO, SCSC and PYLY. *S.minor* is very closely related to *S.sclerotiorum* and expected to bind the probe. Signal intensities >0.07 are written in bold. Correspondence between Oligo ID and species can be found in Table 1.

| Oligo ID | A | B | C | D | E | F |
|---|---|---|---|---|---|---|
| PYSU | 0.01 | 0.00 | 0.00 | −0.01 | −0.01 | −0.01 |
| PYUL | −0.01 | 0.00 | 0.00 | 0.00 | 0.00 | 0.00 |
| RACO | 0.00 | 0.00 | 0.01 | −0.01 | 0.00 | 0.00 |
| RHCE | 0.00 | −0.01 | 0.00 | 0.12 | 0.13 | −0.01 |
| RHFR | 0.02 | 0.01 | 0.02 | 0.00 | 0.00 | 0.00 |
| RHOR | 0.00 | 0.01 | 0.00 | 0.01 | 0.01 | 0.00 |
| RHSE | −0.01 | 0.01 | −0.01 | 0.00 | 0.01 | −0.01 |
| SCBO | 0.00 | 0.00 | 0.02 | 0.01 | −0.01 | 0.03 |
| SCHO | 0.05 | 0.00 | 0.00 | 0.00 | 0.01 | 0.01 |
| SCSC | 0.00 | 0.01 | 0.00 | 0.01 | −0.01 | 0.36 |
| SCTR | 0.07 | 0.01 | 0.00 | 0.01 | 0.02 | 0.01 |
| SEEN | −0.01 | 0.00 | −0.01 | −0.01 | 0.00 | 0.00 |
| SEMA | 0.00 | 0.00 | 0.00 | 0.00 | 0.00 | 0.00 |
| SEPL | −0.01 | 0.00 | −0.01 | −0.01 | −0.01 | 0.00 |
| SETR | 0.00 | 0.01 | 0.00 | 0.01 | 0.00 | 0.00 |
| STAL | 0.00 | 0.00 | 0.01 | 0.01 | 0.00 | 0.00 |
| STGR1 | 0.01 | 0.01 | 0.00 | 0.01 | 0.00 | 0.00 |
| STGR2 | −0.01 | 0.01 | −0.01 | −0.01 | 0.00 | 0.00 |
| STRI | 0.00 | 0.02 | 0.00 | 0.00 | −0.01 | 0.00 |
| STSA | 0.01 | 0.00 | 0.00 | 0.00 | 0.01 | 0.00 |
| STSC | 0.00 | 0.00 | 0.02 | 0.01 | 0.01 | 0.01 |
| THCU | 0.00 | 0.01 | 0.00 | −0.01 | −0.01 | 0.00 |
| TICA | 0.00 | 0.01 | 0.00 | 0.00 | 0.00 | 0.00 |
| TICO | 0.00 | 0.00 | 0.00 | −0.01 | −0.01 | 0.00 |
| TRHA | −0.01 | 0.00 | 0.26 | 0.01 | 0.00 | 0.00 |
| TYIN | 0.00 | −0.01 | 0.00 | 0.00 | 0.00 | 0.00 |
| TYIS1 | 0.00 | 0.00 | 0.01 | 0.01 | 0.01 | 0.00 |
| TYIS2 | 0.00 | −0.01 | −0.01 | −0.01 | −0.01 | −0.01 |
| URDA | 0.00 | 0.01 | 0.01 | 0.01 | 0.01 | 0.00 |
| URTR | 0.00 | −0.01 | −0.01 | 0.01 | 0.00 | 0.00 |
| USMA | 0.00 | 0.00 | 0.00 | 0.01 | −0.01 | 0.01 |
| USNU | −0.01 | 0.00 | 0.00 | 0.01 | −0.01 | 0.00 |
| USST | 0.01 | 0.00 | 0.00 | 0.01 | 0.00 | 0.00 |
| USTR | 0.00 | 0.01 | 0.00 | −0.01 | 0.00 | 0.00 |
| VEDA | 0.14 | 0.63 | 0.56 | 0.79 | 0.78 | 0.01 |
| XATR | −0.01 | 0.00 | 0.01 | 0.00 | 0.00 | 0.00 |
| Biotin-Control | 0.85 | 0.85 | 0.85 | 0.87 | 0.87 | 0.85 |

CONCLUSION

The present invention allows identification of microorganisms from a large selection of fungi and bacterial species. The method according to the invention is faster, has a broader spectrum of microorganisms that can be identified and is more specific than conventional methods.

The invention claimed is:

1. A method for detecting by hybridization techniques at least one pathogen and/or one beneficial microorganism in a sample, said method using at least forty and up to one hundred different nucleic acids, each nucleic acid chosen from (i), (ii) and/or (iii) below:

(i) the sequences selected from the group consisting of:

| Sequence | ID |
|---|---|
| GGGTTGCTTGCTTGCGAGCTCC; | (SEQ ID No 1) |
| CTGGTGTTTGGACTCGCCTTAAAAC; | (SEQ ID No 2) |
| GCACATATTTTGCGCTTTGTATCAGG; | (SEQ ID No 3) |
| TCCGCCAGGGAARACCAAAACTCT; | (SEQ ID No 4) |
| CGGAGCGCGGGCCGTCGCG; | (SEQ ID No 5) |
| ACTTATACCCAAAACGTTGCCTCG; | (SEQ ID No 6) |
| CATTATCGAGTTTACGCTCCATAAC; | (SEQ ID No 7) |
| GCGCAGCTATTAGATCTACGGTG; | (SEQ ID No 8) |
| GCAAGGCTGGAGTATTTTATTACCCT; | (SEQ ID No 9) |
| CCGTGGCCTTGTTGCCACGCCC; | (SEQ ID No 10) |
| ATTGGGGCCTTGTTGCCACACCC; | (SEQ ID No 11) |
| TTTTGCGCTTTGTCCAGTTGCGG; | (SEQ ID No 12) |
| GATTCGTCGCCCCCCCTCCTGG; | (SEQ ID No 13) |
| GACCTTATTCAAACCTTTTTTCAGTT; | (SEQ ID No 14) |
| GCTGTTGGGACCGGCTCACCCG; | (SEQ ID No 15) |
| TGACCGTTGTCACGAGACGACTTTAT; | (SEQ ID No 16) |
| CTTGGTGTTGGGAGCTGCAGTCC; | (SEQ ID No 17) |
| CCATTGCGTAGTAGTAAAACCC; | (SEQ ID No 18) |
| AACGCGCTTCGTTCGGAGGCTT; | (SEQ ID No 19) |
| TTCAACCCTCAAGCCCCGGGTTTG; | (SEQ ID No 20) |
| CGAAGTAGTGATATTCCGCATCGG; | (SEQ ID No 21) |
| GTTAGGGGGTCCCCTCTCCGG; | (SEQ ID No 22) |
| CTCGGTCTCGAGCCGCCGG; | (SEQ ID No 23) |
| ACACCCCATTGAACCTATTTATTTTYAA; | (SEQ ID No 24) |
| ACATCTCGCGCTTTGCATTCAGAA; | (SEQ ID No 25) |
| CGATTTTGGGGGGTGGCTAGTGC; | (SEQ ID No 26) |
| CTCTGAGTACGAAAAGAACCTGAAA; | (SEQ ID No 27) |
| TGCTGGCTCTTCTAGAGTCGGCTC; | (SEQ ID No 28) |
| GGCCAGACGACAGCCATAAACC; | (SEQ ID No 29) |
| CGCCGGTGGACTACCTAAACTCT; | (SEQ ID No 30) |
| CGTCGTCGCTGTTCGCAAGGAC; | (SEQ ID No 31) |
| TCGGGCAACGGAACCAGGCGC; | (SEQ ID No 32) |
| GTTGCCTCGGCGGGCACGGC; | (SEQ ID No 33) |
| CCAGTTATATAGGCACCCAATAAGCC; | (SEQ ID No 34) |
| CACCAAACCAGCTTGGGAAACCTT; | (SEQ ID No 35) |
| GTCACGTGGTCTTGGTTTTGAA; | (SEQ ID No 36) |
| CGCAACCGGGAGCCGCGGCGCGG; | (SEQ ID No 37) |
| TGGACTGGCTTCGGCTAGACTGG; | (SEQ ID No 38) |
| ACCATAGCTCAGTTGCTTGGCTTTT; | (SEQ ID No 39) |
| TGGCGAATGTTTGGACTTCGGTCT; | (SEQ ID No 40) |
| GCGCAAGCTGGGGTGGRCGAG; | (SEQ ID No 41) |
| GAACTTGTGTCTCTGCGGCGCG; | (SEQ ID No 42) |
| AACTGGTGAACCGTAGCTGTGTGGT; | (SEQ ID No 43) |
| CCGTACATTAAACTTGACTTTCTTCC; | (SEQ ID No 44) |
| GGAACTCCACCCTTGAATACACTG; | (SEQ ID No 45) |
| CGACCCCTTTTATAATTCACCCAAC; | (SEQ ID No 46) |
| CTAAAAAACCCCTCATAACCTTTTTTT; | (SEQ ID No 47) |
| CTCCTAAAACCCAATATCTTATTTTTAAG; | (SEQ ID No 48) |
| CAATACTGCCATCTTGTTTTTGAAGG; | (SEQ ID No 49) |
| ATACTTGCCATCTTTTTGGAAGG; | (SEQ ID No 50) |
| CCTAAAAACCCCCCTTATCA; | (SEQ ID No 51) |
| CAACCTTTTTGGAGTATTCTAATGAT; | (SEQ ID No 52) |
| ATACTGCCATCTTATTKAAGGGAGAC; | (SEQ ID No 53) |
| CAGGGCTATCCCCCTGCCAGG; | (SEQ ID No 54) |
| GGAGGGTTGCGCACTTTGTGCGTG; | (SEQ ID No 55) |
| GACGCCCTGTTTTCGGATAGGG; | (SEQ ID No 56) |
| TGGCGTGCGTTTGCTTGCGCTTC; | (SEQ ID No 57) |
| CTATACTCCGAGAACGAAAGTTTTTGG; | (SEQ ID No 58) |
| TAGTAGTGTGTGTRGCACGTTGTC; | (SEQ ID No 59) |
| TGTTTTTGTTTTGTGGAAATACGCTGTTT; | (SEQ ID No 60) |
| GTAGAATTTTGCTGCTCTTGGGCG; | (SEQ ID No 61) |
| CTGTGTAGTCAGGGATGGAATGTGC; | (SEQ ID No 62) |
| TGAACGCATCATGTTGCTTCGGG; | (SEQ ID No 63) |
| CTGGCTTTTGTTTTGGATTTGGAGGT; | (SEQ ID No 64) |
| CAGCGACAACCGACTCTAAGTTCA; | (SEQ ID No 65) |

-continued

| | |
|---|---|
| CTCGTGAAACACATGAAGTCTGAG; | (SEQ ID No 66) |
| TCGGCGCCCCAGGAGAAATCCT; | (SEQ ID No 67) |
| AGTCCATGTCCGCAATGGCAGG; | (SEQ ID No 68) |
| AACACATACCTCTCGTTACAGGGTC; | (SEQ ID No 69) |
| GAGCTGCTCTTCGGGGCCTTGTAT; | (SEQ ID No 70) |
| CTTGTATGCGCGCCAGAGAATATCA; | (SEQ ID No 71) |
| TATTGGGCGTCCGCGGGGA; | (SEQ ID No 72) |
| GCGGAGTTCACGAGCCCTCAC; | (SEQ ID No 73) |
| GCGCCTTGTCTCTCGCGAGAC; | (SEQ ID No 74) |
| AGCTGGATCTCAGTGTTATGCTTGG; | (SEQ ID No 75) |
| GTGCCTCTCGGGGCTTCTGCCG; | (SEQ ID No 76) |
| CCTGTGTAGTAATGCTTAGCTTACAC; | (SEQ ID No 77) |
| CTACGGAGGGGTGGCTGCGTTG; | (SEQ ID No 78) |
| CTACGGAGGGGTGGCTGCGTTG; | (SEQ ID No 79) |
| ACAGCTCTGAGCAAAAATTCAAAATG; | (SEQ ID No 80) |
| GTCCAATGTAGGCGCAGCGTAA; | (SEQ ID No 81) |
| ATTAGCTGGAACCTCTTGTGGACC; | (SEQ ID No 82) |
| CTCATTAAACAATTTTTCTTATAAAGATTG; | (SEQ ID No 84) |
| GTCATTGCACTCAGGTAGACGTAACA; | (SEQ ID No 85) |
| CTTTTTTCTTTTGGAAAAGGTTGACG; | (SEQ ID No 86) |
| ACAGACAATTTTATTGAACACTTTTT; | (SEQ ID No 87) |
| TTTGAAGAGTTGGCGGATCGGTAT; | (SEQ ID No 88) |
| ACGGACAATTTTATTTAACACTTTTG; | (SEQ ID No 89) |
| GCCCTTAAAAKCAGTGGCGGACC; | (SEQ ID No 90) |
| TAATACATGCAAGTCGAGCGGACAGAT; | (SEQ ID No 91) |
| GGGTACTTACCTAATACGTGAGTAT; | (SEQ ID No 92) |
| GAAGGGTARTGTCTTAATACGGCATT; | (SEQ ID No 93) |
| GGAAGGGYAGTGTGTTAATAGCAC; | (SEQ ID No 94) |
| ATGACTGTCCATCGCATGGTGGAT; | (SEQ ID No 95) |
| CTGCGGATCGCATGGTCTGCG; | (SEQ ID No 96) |
| AATACTTCTCCTCGCATGGGGAGG; | (SEQ ID No 97) |
| ATGACACACGACCGCATGGTCTGT; | (SEQ ID No 98) |
| CACCGGAAACGGCCAGAGATGGTCG; and | (SEQ ID No 99) |
| GAGTGTGGTAGAGGATGGCGGAA; | (SEQ ID No 100) |

(ii) sequences having at least 80% identity with SEQ ID NOS:1 through 82 and 84 through 100, or
(iii) the complementary sequences of (i) or (ii),
and hybridizing thereto PCR products obtained from DNAs of pathogens and/or beneficial microorganisms which have been isolated from the sample.

2. The method according to claim 1, wherein the at least one pathogen is selected from bacteria and/or fungi.

3. The method according to claim 2, wherein the at least one fungus and/or bacterium is selected from the group consisting of: *Armillaria mellea, Ascochyta phleina, Bipolaris sorokiniana, Blumeria graminis, Cercospora zebrine, Claviceps purpurea, Colletotrichum trifolii, Corticium fuciforme, Curvularia affinis, Drechslera dictyoides, Drechslera phlei, Drechslera poae, Drechslera siccans, Drechslera tritici-repentis, Epichloe typhina, Exserohilum turcicum, Fusarium culmorum, Fusarium poae, Gaeumannomyces graminis, Gibberella intermedia, Gliocladium catenulatum, Glomerella graminicola, Kabatiella caulivora, Leptosphaeria korrae, Leptosphaerulina australis, Macrophomina phaseolina, Magnaporthe poae, Marasmius oreades, Microdochium bolleyi, Microdochium nivale, Microsphaera trifolii, Myrothecium roridum, Neotyphodium sp., Ophiosphaerella herpotricha, Ophiosphaerella narmari, Peronospora trifoliorum, Phyllachora vulgata, Phytophthora brassicae, Phytophthora cactorum, Phytophthora citricola, Phytophthora drechsleri, Phytophthora fragariae, Phytophthora megasperma, Phytophthora nicotianae, Pseudopeziza medicaginis, Puccinia coronata, Puccinia coronate, Puccinia graminis, Puccinia poae-nemoralis, Puccinia poarum, Puccinia recondite, Puccinia sorghi, Puccinia striiformis, Puccinia triticina, Pyrenochaeta lycopersici, Pythium aphanidermatuma, Pythium debaryanum, Pythium graminicola, Pythium irregulare, Pythium mastophorum, Pythium sulcatum, Pythium ultimum, Ramularia collocygni, Rhizoctonia cerealis, Rhizoctonia fragariae, Rhynchosporium orthosporum, Rhynchosporium secalis, Sclerotinia borealis, Sclerotinia homoeocarpa, Sclerotinia sclerotiorum, Sclerotinia trifoliorum, Septoria macropoda, Septoria tritici, Stemphylium sarcinaeforme, Thanatephorus cucumeris, Thielaviopsis basicola, Thielaviopsis populi, Tilletia caries, Tilletia controversa, Trichoderma hamatum, Typhula incarnate, Typhula ishikariensis, Typhula ishikariensis, Uromyces dactylidis, Uromyces trifolii-repentis, Ustilago maydis, Ustilago nuda, Ustilago striiformis, Ustilago tritici, Verticillium dahliae; Bacillus amyloliquefaciens, Pseudomonas chlororaphis, Serratia entomophila, Serratia plymuthica, Streptomyces albidoflavus, Streptomyces graminofaciens, Streptomyces griseoviridis, Streptomyces rimosus, Streptomyces scabiei,* and *Xanthomonas translucens.*

4. The method according to claim 3 for the detection of all of the fungi and bacteria listed therein.

5. The method according to claim 1, wherein the at least one beneficial microorganism is a plant growth promoting rhizobacteria.

6. The method according to claim 1, wherein the sample is: a turfgrass; soil; natural fertilizer, a natural fertilizer of animal origin, or a natural fertilizer of plant or herbal origin; or seed or crop sample.

7. The method according to claim 6, wherein the sample is a turfgrass root or seed or a blade of turfgrass sample.

8. The method according to claim 6, wherein the turfgrass is selected from the group consisting of Festaceae, Aveneae, Triticeae, Chlorideae, Zoysieae, Paniceae and Andropogoneae Tribe.

9. The method according to claim 1, wherein the hybridization technique is chosen from Microarray-Chip, Southern blotting, Northern blotting, or PCR.

10. The method according to claim 1, wherein the hybridization technique comprises a PCR combined with a Microarray-Chip, wherein the PCR increased the sensitivity, reduces background and/or adds a detection label to the PCR product.

11. A Microarray-Chip consisting of at least forty and up to one hundred different nucleic acids each chosen from (i) and/or (ii) below:

(i) the sequences of SEQ ID NOS: 1 through 82 and 84 through 100, or (ii) the complementary sequences of (i), wherein the nucleic acids are immobilized on the microarray chip.

12. A method for the detection of at least one pathogen and/or beneficial microorganism in a sample comprising the use of a Microarray-Chip according to claim 11.

13. The method according to claim 12, wherein the at least one pathogen is selected from bacteria and/or fungus.

14. The method according to claim 13 wherein the at least one fungus and/or bacterium is selected from the group consisting of: *Armillaria mellea, Ascochyta phleina, Bipolaris sorokiniana, Blumeria graminis, Cercospora zebrine, Claviceps purpurea, Colletotrichum trifolii, Corticium fuciforme, Curvularia affinis, Drechslera dictyoides, Drechslera phlei, Drechslera poae, Drechslera siccans, Drechslera tritici-repentis, Epichloe typhina, Exserohilum turcicum, Fusarium culmorum, Fusarium poae, Gaeumannomyces graminis, Gibberella intermedia, Gliocladium catenulatum, Glomerella graminicola, Kabatiella caulivora, Leptosphaeria korrae, Leptosphaerulina australis, Macrophomina phaseolina, Magnaporthe poae, Marasmius oreades, Microdochium bolleyi, Microdochium nivale, Microsphaera trifolii, Myrothecium roridum, Neotyphodium sp., Ophiosphaerella herpotricha, Ophiosphaerella narmari, Peronospora trifoliorum, Phyllachora vulgata, Phytophthora brassicae, Phytophthora cactorum, Phytophthora citricola, Phytophthora drechsleri, Phytophthora fragariae, Phytophthora megasperma, Phytophthora nicotianae, Pseudopeziza medicaginis, Puccinia coronata, Puccinia coronate, Puccinia graminis, Puccinia poae-nemoralis, Puccinia poarum, Puccinia recondite, Puccinia sorghi, Puccinia striiformis, Puccinia triticina, Pyrenochaeta lycopersici, Pythium aphanidermatuma, Pythium debaryanum, Pythium graminicola, Pythium irregulare, Pythium mastophorum, Pythium sulcatum, Pythium ultimum, Ramularia collo-cygni, Rhizoctonia cerealis, Rhizoctonia fragariae, Rhynchosporium orthosporum, Rhynchosporium secalis, Sclerotinia borealis, Sclerotinia homoeocarpa, Sclerotinia sclerotiorum, Sclerotinia trifoliorum, Septoria macropoda, Septoria tritici, Stemphylium sarcinaeforme, Thanatephorus cucumeris, Thielaviopsis basicola, Thielaviopsis populi, Tilletia caries, Tilletia controversa, Trichoderma hamatum, Typhula incarnate, Typhula ishikariensis, Typhula ishikariensis, Uromyces dactylidis, Uromyces trifolii-repentis, Ustilago maydis, Ustilago nuda, Ustilago striiformis, Ustilago tritici, Verticillium dahliae; Bacillus amyloliquefaciens, Pseudomonas chlororaphis, Serratia entomophila, Serratia plymuthica, Streptomyces albidoflavus, Streptomyces graminofaciens, Streptomyces griseoviridis, Streptomyces rimosus, Streptomyces scabiei,* and *Xanthomonas translucens.*

15. The method according to claim 13 for the detection of all of the fungi and bacteria listed therein.

16. The method according to claim 12, wherein the at least one beneficial microorganism is a plant growth promoting rhizobacterium.

17. The method according to claim 12, wherein the sample is: a turfgrass; soil; natural fertilizer, a natural fertilizer of animal origin, or a natural fertilizer of plant or herbal origin; or seed or crop sample.

18. The method according to claim 17, wherein the sample is a turfgrass root or seed or a blade of turfgrass sample.

19. The method according to claim 17, wherein the turfgrass is selected from the group consisting of Festaceae, Aveneae, Triticeae, Chlorideae, Zoysieae, Paniceae and Andropogoneae Tribe.

20. A detection method of pathogens and/or beneficial microorganisms in an organic sample, comprising the steps of:

a) DNA isolation from the sample and from standards comprising DNA of said pathogens and/or beneficial microorganisms;

b) amplification of the isolated DNAs of step a) by PCR;

c) hybridization of the PCR products obtained, on a Microarray-Chip as defined in claim 11;

d) detection of the bounded DNAs; and e) deduction therefrom if the sample contains pathogens and/or beneficial microorganisms.

21. The method according to claim 20, wherein the pathogens to be detected are selected from bacteria and/or fungi.

22. The method according to claim 21, wherein fungi and/or bacteria are selected from the group consisting of: *Armillaria mellea, Ascochyta phleina, Bipolaris sorokiniana, Blumeria graminis, Cercospora zebrine, Claviceps purpurea, Colletotrichum trifolii, Corticium fuciforme, Curvularia affinis, Drechslera dictyoides, Drechslera phlei, Drechslera poae, Drechslera siccans, Drechslera tritici-repentis, Epichloe typhina, Exserohilum turcicum, Fusarium culmorum, Fusarium poae, Gaeumannomyces graminis, Gibberella intermedia, Gliocladium catenulatum, Glomerella graminicola, Kabatiella caulivora, Leptosphaeria korrae, Leptosphaerulina australis, Macrophomina phaseolina, Magnaporthe poae, Marasmius oreades, Microdochium bolleyi, Microdochium nivale, Microsphaera trifolii, Myrothecium roridum, Neotyphodium sp., Ophiosphaerella herpotricha, Ophiosphaerella narmari, Peronospora trifoliorum, Phyllachora vulgata, Phytophthora brassicae, Phytophthora cactorum, Phytophthora citricola, Phytophthora drechsleri, Phytophthora fragariae, Phytophthora megasperma, Phytophthora nicotianae, Pseudopeziza medicaginis, Puccinia coronata, Puccinia coronate, Puccinia graminis, Puccinia poae-nemoralis, Puccinia poarum, Puccinia recondite, Puccinia sorghi, Puccinia striiformis, Puccinia triticina, Pyrenochaeta lycopersici, Pythium aphanidermatuma, Pythium debaryanum, Pythium graminicola, Pythium irregulare, Pythium mastophorum, Pythium sulcatum, Pythium ultimum, Ramularia collo-cygni, Rhizoctonia cerealis, Rhizoctonia fragariae, Rhynchosporium orthosporum, Rhynchosporium secalis, Sclerotinia borealis, Sclerotinia homoeocarpa, Sclerotinia sclerotiorum, Sclerotinia trifoliorum, Septoria macropoda, Septoria tritici, Stemphylium sarcinaeforme, Thanatephorus cucumeris, Thielaviopsis basicola, Thielaviopsis populi, Tilletia caries, Tilletia controversa, Trichoderma hamatum, Typhula incarnate, Typhula ishikariensis, Typhula ishikariensis, Uromyces dactylidis, Uromyces trifolii-repentis, Ustilago maydis, Ustilago nuda, Ustilago striiformis, Ustilago tritici, Verticillium dahliae; Bacillus amyloliquefaciens, Pseudomonas chlororaphis, Serratia entomophila, Serratia plymuthica, Streptomyces albidoflavus, Streptomyces graminofaciens, Streptomyces griseoviridis, Streptomyces rimosus, Streptomyces scabiei,* and *Xanthomonas translucens.*

23. The method according to claim 22 for detection of all of the fungi and bacteria listed therein, wherein two PCRs are conducted in step b), the first directed to fungus DNAs and the second directed to bacterial DNAs.

24. The method according to claim 23, wherein the two PCRs are combined into one single reaction tube.

25. The method according to claim 20, wherein the beneficial microorganisms are plant growth promoting rhizobacteria.

26. The method according to claim 20 for screening samples before its use for absence of pathogens.

27. A kit for the detection of pathogens and/or beneficial microorganisms in an organic sample comprising nucleic acids, wherein the nucleic acids consist of at least forty and up to one hundred different nucleic acids each chosen from (i) and/or (ii) below:
(i) the nucleic acids of sequences: SEQ ID NOS: 1 through 82 and 84 through 100, or
(ii) the nucleic acids of complementary sequences of (i), wherein the nucleic acids have been labeled.

28. A method of treating a diseased turfgrass comprising the steps of:
a) detecting by a method combining PCR and Microarray-Chip the absence or the presence of nucleic acids from at least one pathogenic fungus and/or bacterium in a sample of soil in which the diseased turfgrass is growing, or in a sample of the diseased turfgrass, by hybridization of PCR products with at least forty and up to one hundred different nucleic acids, each nucleic acid chosen from (i), (ii) and/or (iii) below:
(i) the sequences selected from the group consisting of:

| Sequence | ID |
|---|---|
| GGGTTGCTTGCTTGCGAGCTCC; | (SEQ ID NO: 1) |
| CTGGTGTTTGGACTCGCCTTAAAAC; | (SEQ ID NO: 2) |
| GCACATATTTTGCGCTTTGTATCAGG; | (SEQ ID NO: 3) |
| TCCGCCAGGGAARACCAAAACTCT; | (SEQ ID NO: 4) |
| CGGAGCGCGGGCCGTCGCG; | (SEQ ID NO: 5) |
| ACTTATACCCAAAACGTTGCCTCG; | (SEQ ID NO: 6) |
| CATTATCGAGTTTACGCTCCATAAC; | (SEQ ID NO: 7) |
| GCGCAGCTATTAGATCTACGGTG; | (SEQ ID NO: 8) |
| GCAAGGCTGGAGTATTTTATTACCCT; | (SEQ ID NO: 9) |
| CCGTGGCCTTGTTGCCACGCCC; | (SEQ ID NO: 10) |
| ATTGGGGCCTTGTTGCCACACCC; | (SEQ ID NO: 11) |
| TTTTGCGCTTTGTCCAGTTGCGG; | (SEQ ID NO: 12) |
| GATTCGTCGCCCCCCCTCCTGG; | (SEQ ID NO: 13) |
| GACCTTATTCAAACCTTTTTTTCAGTT; | (SEQ ID NO: 14) |
| GCTGTTGGGGACCGGCTCACCCG; | (SEQ ID NO: 15) |
| TGACCGTTGTCACGAGACGACTTTAT; | (SEQ ID NO: 16) |
| CTTGGTGTTGGGAGCTGCAGTCC; | (SEQ ID NO: 17) |
| CCATTGCGTAGTAGTAAAACCC; | (SEQ ID NO: 18) |
| AACGCGCTTCGTTCGGAGGCTT; | (SEQ ID NO: 19) |
| TTCAACCCTCAAGCCCCGGGTTTG; | (SEQ ID NO: 20) |
| CGAAGTAGTGATATTCCGCATCGG; | (SEQ ID NO: 21) |
| GTTAGGGGGTCCCCTCTCCGG; | (SEQ ID NO: 22) |
| CTCGGTCTCGAGCCGCCGG; | (SEQ ID NO: 23) |
| ACACCCCATTGAACCTATTTATTTTYAA; | (SEQ ID NO: 24) |
| ACATCTCGCGCTTTGCATTCAGAA; | (SEQ ID NO: 25) |
| CGATTTTGGGGGTGGCTAGTGC; | (SEQ ID NO: 26) |
| CTCTGAGTACGAAAAGAACCTGAAA; | (SEQ ID NO: 27) |
| TGCTGGCTCTTCTAGAGTCGGCTC; | (SEQ ID NO: 28) |
| GGCCAGACGACAGCCATAAACC; | (SEQ ID NO: 29) |
| CGCCGGTGGACTACCTAAACTCT; | (SEQ ID NO: 30) |
| CGTCGTCGCTGTTCGCAAGGAC; | (SEQ ID NO: 31) |
| TCGGGCAACGGAACCAGGCGC; | (SEQ ID NO: 32) |
| GTTGCCTCGGCGGGCACGGC; | (SEQ ID NO: 33) |
| CCAGTTATATAGGCACCCAATAAGCC; | (SEQ ID NO: 34) |
| CACCAAACCAGCTTGGGAAACCTT; | (SEQ ID NO: 35) |
| GTCACGTGGTCTTGGTTTTGAA; | (SEQ ID NO: 36) |
| CGCAACCGGGAGCCGCGGCGCGG; | (SEQ ID NO: 37) |
| TGGACTGGCTTCGGCTAGACTGG; | (SEQ ID NO: 38) |
| ACCATAGCTCAGTTGCTTGGCTTTT; | (SEQ ID NO: 39) |
| TGGCGAATGTTTGGACTTCGGTCT; | (SEQ ID NO: 40) |
| GCGCAAGCTGGGGTGGRCGAG; | (SEQ ID NO: 41) |
| GAACTTGTGTCTCTGCGGCGCG; | (SEQ ID NO: 42) |
| AACTGGTGAACCGTAGCTGTGTGGT; | (SEQ ID NO: 43) |
| CCGTACATTAAACTTGACTTTCTTCC; | (SEQ ID NO: 44) |
| GGAACTCCACCCTTGAATACACTG; | (SEQ ID NO: 45) |
| CGACCCCTTTTATAATTCACCCAAC; | (SEQ ID NO: 46) |
| CTAAAAAACCCCTCATAACCTTTTTTT; | (SEQ ID NO: 47) |
| CTCCTAAAACCCAATATCTTATTTTTAAG; | (SEQ ID NO: 48) |
| CAATACTGCCATCTTGTTTTTGAAGG; | (SEQ ID NO: 49) |
| ATACTTGCCATCTTTTTGGAAGG; | (SEQ ID NO: 50) |
| CCTAAAAACCCCCCTTATCA; | (SEQ ID NO: 51) |
| CAACCTTTTTGGAGTATTCTAATGAT; | (SEQ ID NO: 52) |
| ATACTGCCATCTTATTKAAGGGAGAC; | (SEQ ID NO: 53) |
| CAGGGCTATCCCCCTGCCAGG; | (SEQ ID NO: 54) |
| GGAGGGTTGCGCACTTTGTGCGTG; | (SEQ ID NO: 55) |
| GACGCCCTGTTTTCGGATAGGG; | (SEQ ID NO: 56) |
| TGGCGTGCGTTTGCTTGCGCTTC; | (SEQ ID NO: 57) |
| CTATACTCCGAGAACGAAAGTTTTGG; | (SEQ ID NO: 58) |
| TAGTAGTGTGTGTRGCACGTTGTC; | (SEQ ID NO: 59) |
| TGTTTTTGTTTTGTGGAAATACGCTGTTT; | (SEQ ID NO: 60) |
| GTAGAATTTTGCTGCTCTTGGGCG; | (SEQ ID NO: 61) |
| CTGTGTAGTCAGGGATGGAATGTGC; | (SEQ ID NO: 62) |
| TGAACGCATCATGTTGCTTCGGG; | (SEQ ID NO: 63) |
| CTGGCTTTTGTTTTGGATTTGGAGGT; | (SEQ ID NO: 64) |
| CAGCGACAACCGACTCTAAGTTCA; | (SEQ ID NO: 65) |

| | |
|---|---|
| CTCGTGAAACACATGAAGTCTGAG; | (SEQ ID NO: 66) |
| TCGGCGCCCCAGGAGAAATCCT; | (SEQ ID NO: 67) |
| AGTCCATGTCCGCAATGGCAGG; | (SEQ ID NO: 68) |
| AACACATACCTCTCGTTACAGGGTC; | (SEQ ID NO: 69) |
| GAGCTGCTCTTCGGGGCCTTGTAT; | (SEQ ID NO: 70) |
| CTTGTATGCGCGCCAGAGAATATCA; | (SEQ ID NO: 71) |
| TATTGGGCGTCCGCGGGGGA; | (SEQ ID NO: 72) |
| GCGGAGTTCACGAGCCCTCAC; | (SEQ ID NO: 73) |
| GCGCCTTGTCTCTCGCGAGAC; | (SEQ ID NO: 74) |
| AGCTGGATCTCAGTGTTATGCTTGG; | (SEQ ID NO: 75) |
| GTGCCTCTCGGGGCTTCTGCCG; | (SEQ ID NO: 76) |
| CCTGTGTAGTAATGCTTAGCTTACAC; | (SEQ ID NO: 77) |
| CTACGGAGGGGTGGCTGCGTTG; | (SEQ ID NO: 78) |
| CTACGGAGGGGTGGCTGCGTTG; | (SEQ ID NO: 79) |
| ACAGCTCTGAGCAAAAATTCAAAATG; | (SEQ ID NO: 80) |
| GTCCAATGTAGGCGCAGCGTAA; | (SEQ ID NO: 81) |
| ATTAGCTGGAACCTCTTGTGGACC; | (SEQ ID NO: 82) |
| CTCATTAAACAATTTTTCTTATAAAGATTG; | (SEQ ID NO: 84) |
| GTCATTGCACTCAGGTAGACGTAACA; | (SEQ ID NO: 85) |
| CTTTTTTCTTTTGGAAAAGGTTGACG; | (SEQ ID NO: 86) |
| ACAGACAATTTTATTGAACACTTTTT; | (SEQ ID NO: 87) |
| TTTGAAGAGTTGGCGGATCGGTAT; | (SEQ ID NO: 88) |
| ACGGACAATTTTATTTAACACTTTTG; | (SEQ ID NO: 89) |
| GCCCTTAAAAKCAGTGGCGGACC; | (SEQ ID NO: 90) |
| TAATACATGCAAGTCGAGCGGACAGAT; | (SEQ ID NO: 91) |
| GGGTACTTACCTAATACGTGAGTAT; | (SEQ ID NO: 92) |
| GAAGGGTARTGTCTTAATACGGCATT; | (SEQ ID NO: 93) |
| GGAAGGGYAGTGTGTTAATAGCAC; | (SEQ ID NO: 94) |
| ATGACTGTCCATCGCATGGTGGAT; | (SEQ ID NO: 95) |
| CTGCGGATCGCATGGTCTGCG; | (SEQ ID NO: 96) |
| AATACTTCTCCTCGCATGGGGAGG; | (SEQ ID NO: 97) |
| ATGACACACGACCGCATGGTCTGT; | (SEQ ID NO: 98) |
| CACCGGAAACGGCCAGAGATGGTCG; and | (SEQ ID NO: 99) |
| GAGTGTGGTAGAGGATGGCGGAA; | (SEQ ID NO: 100) |

(ii) sequences having at least 80% identity with SEQ ID NOS:1 through 82 and 84 through 100, or
(iii) the complementary sequences of (i) or (ii);
b) if nucleic acids from one or more pathogenic fungi and/or bacteria have been detected in step a), selecting one or more antifungal and/or antibacterial agents which target the one or more pathogenic fungi and/or bacteria from which nucleic acids have been detected; and
c) applying the selected one or more antifungal and/or antibacterial agents of step b) to the diseased turfgrass.

\* \* \* \* \*